(12) United States Patent
Taicher et al.

(10) Patent No.: US 7,366,560 B2
(45) Date of Patent: Apr. 29, 2008

(54) NUCLEAR MAGNETIC RESONANCE METHOD FOR BODY COMPOSITION ANALYSIS

(75) Inventors: Gersh Z. Taicher, Houston, TX (US); Arcady Reiderman, Houston, TX (US); Israel Kovner, Houston, TX (US)

(73) Assignee: Echo Medical Systems, LLC, Houston, TX (US)

( * ) Notice: Subject to any disclaimer, the term of this patent is extended or adjusted under 35 U.S.C. 154(b) by 329 days.

(21) Appl. No.: 11/133,104

(22) Filed: May 19, 2005

(65) Prior Publication Data

US 2006/0293587 A1 Dec. 28, 2006

(51) Int. Cl.
*A61B 5/05* (2006.01)
(52) U.S. Cl. ........................... 600/410; 324/307
(58) Field of Classification Search ............. 600/410; 356/302, 311, 319, 326; 324/307–309
See application file for complete search history.

(56) References Cited

U.S. PATENT DOCUMENTS

| | | | | |
|---|---|---|---|---|
| 5,262,724 A | * | 11/1993 | Tanttu | 324/309 |
| 5,517,115 A | * | 5/1996 | Prammer | 324/303 |
| 5,644,232 A | * | 7/1997 | Smith | 324/304 |
| 6,147,492 A | * | 11/2000 | Zhang et al. | 324/309 |

* cited by examiner

Primary Examiner—Eric F. Winakur
Assistant Examiner—Michael Rozanski
(74) Attorney, Agent, or Firm—Richard A Fagin

(57) ABSTRACT

A method is disclosed for analyzing composition of a body part from nuclear magnetic resonance measurements made on the body part. The method includes exciting a predetermined sequence of nuclear magnetic resonance phenomena in the body part and measuring nuclear magnetic resonance signals from the body part. At least a part of the measured signals are composed into a measurement vector. The mass of the at least one constituent is determined as a predetermined function of the measurement vector. The predetermined function represents the at least one constituent and defines a standard for a range of at least one compositional variations and temperature variations of the at least one constituent.

29 Claims, 17 Drawing Sheets

NUCLEAR MAGNETIC RESONANCE METHOD FOR BODY COMPOSITION ANALYSIS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention is related to the field of Nuclear Magnetic Resonance (NMR) and Magnetic Resonance Imaging (MRI) apparatus and methods. More particularly, the invention relates to apparatus and methods for determining a known component from a mixture of unknown components. More specifically, the invention relates to methods and apparatus for using NMR for precise and quantitative determination of material composition. In one application methods and apparatus according to the invention relate to using NMR for rapid, quantitative in-vivo determination of tissue properties, such as Fat-to-Lean ratio.

2. Background Art

The description of the invention and its background are explained herein in the context of Fat-to-Lean ratio determination. It is to be explicitly understood, however, that the invention is not limited to analysis and monitoring of Fat-to-Lean ratio. For example, Fat-to-Lean-to-Bone ratio may also be determined using methods and apparatus according to the invention. Fat composition (different fatty acids), lean composition (water, protein, and glycogen), and bone composition (mineral, collagen, and water) may also be determined using methods and apparatus according to the invention.

In human health monitoring and treatment, the level of total body mass that is derived from adipose mass is the variable that has been determined empirically to be most closely associated with risk for pathology. Advanced models of body composition and newer technologies that precisely and accurately calculate adipose mass may eventually replace simple anthropometric methods such as body weight, height, waist circumference, skin fold thickness, etc. in determining likelihood of pathology.

Body Mass Index (BM) is defined as body weight (kg)/height$^2$ (m$^2$). Although BMI is a reasonable marker of energy balance for individuals, it is very rough marker of adiposity across populations.

Hydrostatic weighing or Under Water Weighing (UWW) has been the most preferred technique for human whole body composition analysis for several decades. However, due to several practical inconveniences and questionable underlying assumptions its usage is limited. UWW assess whole body fat content expressed as a percentage of body weight. See, for example, U.S. Pat. No. 4,873,866 to Fairbanks.

UWW based on a two-component (2C) body composition model assumes specific densities 0.9 and 1.1 g/cm$^3$ for Fat Mass (FM) and Fat-Free Mass (FFM) respectively. UWW further assumes that these densities are constant within different individuals or populations. Whole body densities have been determined to vary in a range between 1.08 g/cm$^3$ (very lean) and 1.00 g/cm$^3$ (severely obese).

Other UWW techniques are based on four-component (4C) or three-component (3C) body composition models. 4C and 3C models additionally use assumptions that FFM is composed of constant proportions of water (73.2%), minerals (6.8%), and protein (19.5%) each having a specific density assumed to be constant at body temperature. Precise measurement of Total Body Water (TBW) and Bone Mineral Content (BMC) are required to use 4C and 3C models because of the potential for additional error in the final results for FM that is related to TBW and BMC measurements. In certain human population groups, such as children, the elderly, African-Americans, or sick patients, 4C or 3C methods may provide more accurate estimates of FM than the 2C method.

UWW is not practical for accurate measurements in individuals having cardiovascular or pulmonary disorders, elderly, young children, and very obese subjects. Substantial errors may occur due to body movement and the buoyant effects of air in the gastrointestinal tract and lungs. The simultaneous measurement of residual lung volume and underwater weight may be preferred because it controls for the effects of the increased pressure of water on the thorax during immersion. Inaccurate measurements of air in the lungs can be a major source of error when estimating body density from underwater weighing. However, UWW may be the only practical method of measuring body fat in very obese subjects who cannot be evaluated by other methods.

U.S. Pat. No. 4,144,763 to Vogelman and U.S. Pat. No. 5,105,825 to Dempster disclose plethysmography apparatuses and methods. Plethysmography is a more convenient way for measuring body adiposity as compared to UWW. Measurement of body density by plethysmography allows for a high degree of precision in volume measurement, but inconsistencies in body density, the necessity for lung volume correction, variation in skeletal mass, and degree of hydration are not accounted for by plethysmography methods.

U.S. Pat. No. 6,393,317 to Fukuda et al. and U.S. Pat. No. 5,415,176 to Sato et al. disclose two examples of widely used techniques for fat assessment based on body bioelectrical impedance. A method for fat assessment based on body electrical conductivity is described by Unangst E. T., Jr., and Merkley L. A. in, *The effects of lipid location on non-invasive estimates of body composition using EM-SCAN technology*, J. Exp. Biol., 2002:205 (Pt. 19) pp. 3101-3105.

None of the foregoing methods of body composition analysis have been broadly implemented, largely because of inaccuracy and poor specificity of the results. Measurement of body composition of experimental animals by plethysmography, hydrostatic weighing (UWW), bioelectrical impedance, and electrical conductivity has not proven to be practical.

In order to provide a more precise quantitative measure of whole body composition in animals, the Dual Energy X-ray Absorptiometry (DEXA) technique is more widely used than the foregoing techniques. U.S. Pat. No. 6,233,473 to Shepherd et al. discloses a method of body composition analysis using a dual-energy, fan-shaped distribution of X-rays, and detector signal processing that corrects for mass magnification and other effects due to the geometry of the measurement system. In the method disclosed in the '473 patent, the thickness of the attenuating material along respective ray paths is obtained by using a four-dimensional look-up table derived experimentally from step-wedge measurements, and another look-up table and interpolation between table entries are used to convert projected mass to true mass.

DEXA precision differs with the instrument type, the particular animal species being evaluated, the software and the actual methods that are used. The basic physical principle of DEXA is associated with attenuation of X-rays transmitted through an object. The degree of attenuation (attenuation coefficient) depends on the object's thickness, density, and chemical composition as well as the initial energy of the X-ray photons. At low initial photon energies (less than about 0.8 million electron volts), photon attenuation is non-linear, and is governed by the photoelectric effect and by Compton scattering. If the object under evaluation is composed of two or more homogeneous materials, then the composite attenuation coefficient may be approximated by a weighted sum of the individual attenuation coefficients, each weighted for its fractional contribution to the total mass.

The attenuation of X-rays through lean human body tissue and fat tissue is slightly different, but is substantially different for bone tissue, primarily because of their differences in density and chemical composition. DEXA does not provide three independent measurements, even though three body composition values: bone; lean; and fat tissue fractional amounts are reported. With increasing initial photon energy, the differences in the attenuation properties for these three types of body tissue decrease.

The following is summary of a DEXA technique for whole body composition analysis of laboratory mice. First, a record is made of the attenuation of X-rays at both initial photon energy values in air. Then the pixel size, scanning speed and beam size are selected. A scan of the object (mouse) is then made. The detected X-ray photon amplitudes and count rates are corrected for detector dead time loss, spill-over from one energy window to another, and for beam hardening. From two equations (two photon energy levels) the amount of soft tissue and bone mineral is then determined.

Soft tissue in the non-bone pixels is separated into fat and lean mass by means of a calibration that translates attenuation coefficients into fat fractions. Corrections are made for tissue thickness variation. The fat content of the soft tissue layer overlying, underlying and/or inside bone is estimated based on predetermined relationships between fat-to-lean ratio of pure soft tissue surrounding bone.

The main advantage of DEXA is the ability to analyze individual regions within an entire body. DEXA as a method for analyzing whole body composition may be subject to the following limitations. First is the assumption that the composition of the soft tissue layer overlying bone has the same Fat-to-Lean ratio, or the ratio is related in a predetermined way to the Fat-to-Lean ratio of other non-bone tissues. For a whole body scan, about 40% of the pixels are typically classified as containing bone. Next, thicker tissue regions remove more low energy photons from the radiation beam as compared to thinner regions, this effect being known as "beam hardening." Further, DEXA assumes homogeneous hydration of lean tissues.

In the field of in-vivo analysis of body composition parameters there have been numerous attempts to use Nuclear Magnetic Resonance (NMR) methods and apparatus. Briefly, these techniques and their limitations are as follows.

I. Magnetic Resonance Spectroscopy (MRS). The MRS method used to quantify fat content in a body is based on recording a $^1$H (proton) spectrum in-vivo. An example of using a standard MRS apparatus for such analysis is described by Mystkowski et al. in, *Validation of whole-body magnetic resonance spectroscopy as a tool to assess murine body composition*", Int. J. of Obesity, 2000:24, pp. 719-724. A drawback to the technique disclosed in the Mystkowski et al. paper is the fact that many human tissue types contain a variety of lipids which yield $^1$H spectral peaks within a very narrow chemical shift range. In addition, MRS requires very high homogeneity and strength of the static magnetic field, due to the required high spectral resolution of chemical shifts, making MRS equipment that would be used for whole body composition analysis extremely expensive.

II. Magnetic Resonance Imaging (MRI). A MRI method for body composition analysis is described by Ross et al. in, *Quantification of adipose tissue by MRI: relationship with anthropometric variables*, J. Appl. Physiol. 1992:72(2) pp. 787-795, and in U.S. Pat. Nos. 5,225,781; 5,594,336; 6,147, 492; and 5,644,232.

III. NMR Relaxometry. NMR relaxometry methods known in the art avoid the necessity for complicated and expensive equipment. NMR relaxometry methods known in the art, however, have several limitations, such as with respect to accuracy and precision. Kamman et al., *Multi-exponential relaxation analysis with MR imaging and NMR spectroscopy using fat-water systems*, Magn. Reson. Imaging 1987:5(5) pp. 381-392 describes a NMR relaxometry method for body composition analysis. Despite extensive research and development into methods of whole body composition analysis, there is still a need for reliable, accurate, precise, and specific non-invasive methods for acquiring information relating to body fat mass, lean mass, total water content, etc.

Furthermore, methods known in the art for composition analysis from NMR measurements, such as Carr-Purcell-Meiboom-Gill sequence spin echo amplitude measurements, typically use multicomponent exponential decay decomposition to determine the fractional amounts of selected components in the body or other material being analyzed. Such methods are not particularly suitable for use with some types of NMR apparatus for body composition analysis because of the relatively low radio frequency used for the RF magnetic field (associated with the relatively low amplitude static magnetic field). There are only small differences in the amplitude decay of spin echo measurements for the various components of a body being analyzed, and as a result, it has proven necessary to develop different techniques for analyzing body composition from NMR measurements.

SUMMARY OF THE INVENTION

One aspect of the invention is a method for analyzing composition of a body part from nuclear magnetic resonance measurements made on the body part. The method according to this aspect includes exciting a predetermined sequence of nuclear magnetic resonance phenomena in the body part and measuring nuclear magnetic resonance signals from the body part. At least a part of the measured signals are composed into a measurement vector. The mass of the at least one constituent is calculated as a predetermined function of the measurement vector. The predetermined function represents the at least one constituent and defines a standard for a range of compositional and/or temperature variations of the at least one constituent.

Another aspect of the invention is a method for determining an amount of fat in a body part from nuclear magnetic resonance measurements made on the body part. A method according to this aspect of the invention includes calculating the total amount of fat as a predetermined function of the nuclear magnetic resonance measurements, the function representing a standard for the fat.

Other aspects and advantages of the invention will be apparent from the following description and the appended claims.

DETAILED DESCRIPTION

The description of the invention first includes a description of an example apparatus for making nuclear magnetic resonance measurements for body composition analysis. Following the description of the example apparatus is a description of embodiments of methods for analyzing the measurements made by the example apparatus to determine the body composition. "Body composition analysis" as used in this description generally refers to determining a mass or mass fraction of one or more selected constituents of the body or a part of the body being analyzed. Finally, an alternative embodiment of an apparatus is described. The alternative apparatus includes elements adapted to select a particular part of the body for analysis by localizing nuclear magnetic resonance excitation and detection to within a part of the body. The same composition analysis methods described with respect to the first apparatus may be used with measurements made using the alternative apparatus, or even with conventional magnetic resonance imaging apparatus, as will be explained below.

1. Nuclear Magnetic Resonance Measurement Apparatus

Figure 1:
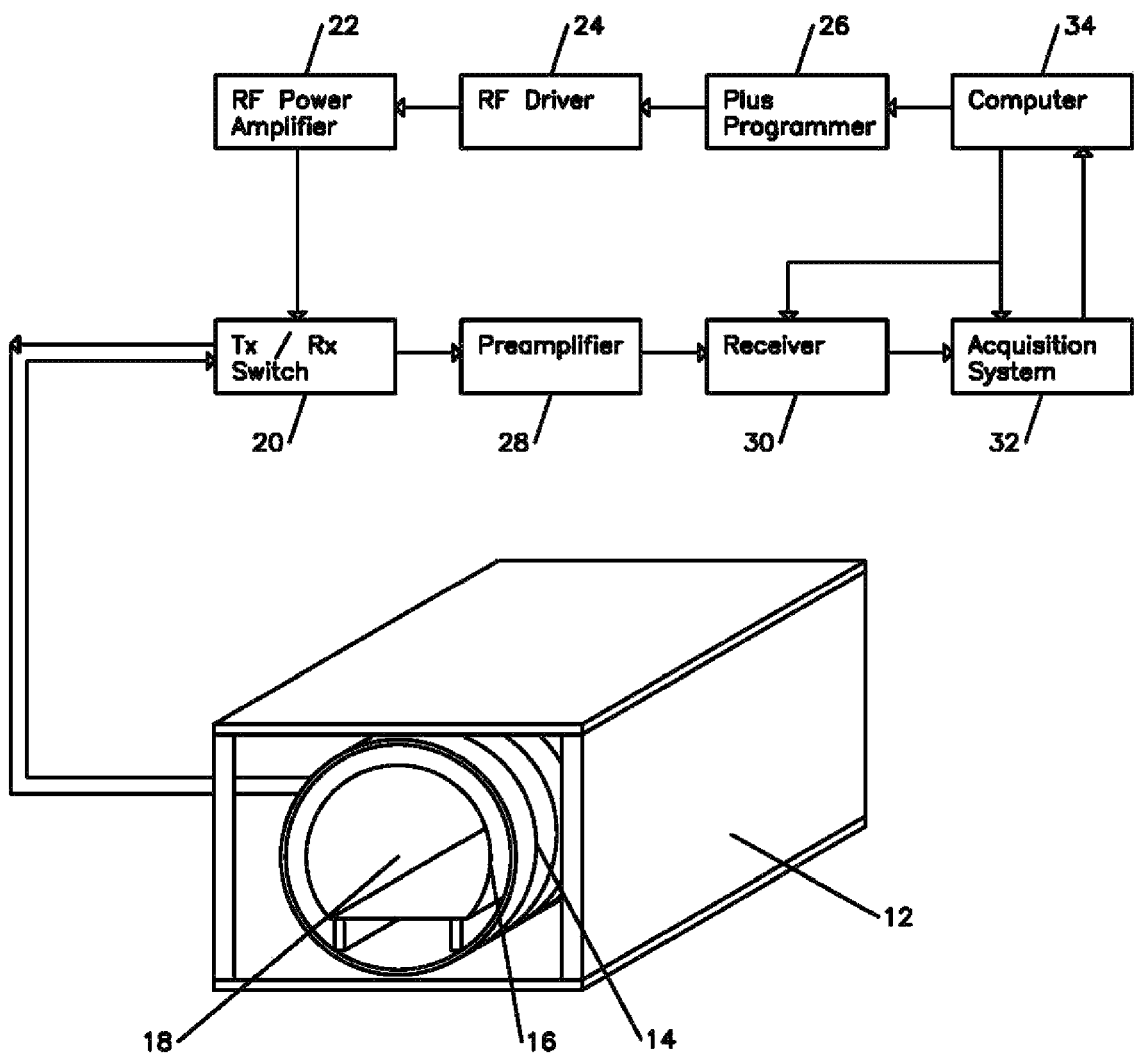
FIG. 1 shows one embodiment of a NMR apparatus that can be used with methods according to the invention.

An example nuclear magnetic resonance (NMR) apparatus is shown generally in FIG. 1 at 10. The apparatus 10 includes a magnet 12 disposed around or on opposed sides of a sample chamber 18. The magnet 12 may be a permanent magnet, or an electromagnet, and is configured to induce a substantially homogeneous static magnetic field within the sample chamber 18. The volume of the sample chamber 18 may be defined by an enclosure such as a polycarbonate tube or box, shown generally at 16 in FIG. 1. The purpose of defining the chamber volume using the enclosure 16 is to precisely set the geometric boundaries of the volume in space within which a body being analyzed may move, substantially without affecting accuracy of NMR measurements performed according to the invention. The enclosure 16 may be made from any substantially electrically non-conductive and nonmagnetic material known in the art.

A radio frequency (RF) antenna 14 is disposed about the enclosure 16, typically on the exterior surface of the enclosure 16. In the present embodiment, the antenna 14 comprises a wire coil wound so that its turns lie in planes substantially perpendicular to the longitudinal axis of the chamber 18. When pulses of RF electrical power are passed through the antenna 14, an RF magnetic field is induced within the chamber 18. Although described above in terms of coils, the antenna 14 can be configured in any other way as long as the RF magnetic field induced by the antenna 14 is substantially perpendicular to the static magnetic field induced by the magnet 12 within the volume defined by the chamber 18.

The antenna 14 performs both RF transmit and RF receive functions, and is coupled to a T/R matching circuit and switch 20. The switch 20 is under control of a computer 34 or similar programmable controller configured to operate the switch 20 such that the antenna 14 is selectively coupled to an RF power amplifier 22 during RF pulse transmission intervals, or to a receiver preamplifier 28 during NMR signal detection (receive) intervals. The input of the RF power amplifier 22 is coupled to an RF driver 24, the input of which is itself coupled to a pulse programmer 26. The pulse programmer 26 may be a separate element under control of the computer, 34 or may be a function performed by the computer 34 itself.

The receiver preamplifier 28 is coupled to an RF receiver 30, which is itself coupled to an acquisition system 32. The acquisition system may include analog to digital converters, digital filters and a recording device (not shown separately). The output of the acquisition system 32 is coupled to the computer 34 for analysis of voltages detected by the antenna 14 resulting from NMR phenomena in an object (not shown in FIG. 1) disposed in the chamber 18.

The pulse programmer 26 is configured to operate the RF driver 24 to cause generation of a succession of selected length and selected frequency RF pulses through the antenna 14, such that NMR phenomena are induced in the object (not shown). As is well known in the art, the frequency, amplitude and duration of the RF pulses are related to the amplitude of the static magnetic field within the chamber 18, and to the Larmor frequency of nuclei which are excited within the object (not shown) for NMR relaxometry analysis. For composition analysis of human and other animal bodies, the nuclei are typically protons ($^1$H).

In the present embodiment, the RF pulse amplitude and duration can be selected to provide first approximately 90 degree (transverse) reorientation of magnetic spin axes of protons in the object (not shown) and then a succession of 180 degree (inverse or refocusing) magnetic spin reorientations. Each refocusing pulse is typically followed by a time interval during which the antenna 14 is coupled to the receiver pre amplifier 28 for detecting NMR phenomena from the object (not shown). Such sequences of transverse reorientation, inverse reorientation and NMR signal detection are well known in the art for determining transverse relaxation time ($T_2$) and longitudinal relaxation time ($T_1$) of materials being analyzed.

In the example apparatus of FIG. 1, if certain requirements are met for the amount of spatial variation of the static and RF magnetic fields within the sample chamber 18, and requirements for the excitation spectrum of the RF magnetic field, high measurement precision can be obtained without the need to build a measuring apparatus of excessive size and cost. At the same time, apparatus and methods according to the invention which meet such requirements of magnetic field distribution and RF field spectral content are fully able to make precise measurements of whole body composition of, for example, a live, conscious animal, even if the body being analyzed moves within the chamber 18. An apparatus as shown in FIG. 1 makes practical analysis of living, conscious animals, including humans, for whole body composition without the need for large, expensive NMR relaxometry or MRI (imaging) systems.

In order to explain the function of the apparatus, factors which affect the accuracy of NMR measurements will be explained. An expression for the NMR signal amplitude S(t) induced in an NMR receiver antenna (e.g., antenna 14 in FIG. 1) as a result of inducing NMR phenomena in an object or body being analyzed is as follows:

$$S(t) = \int_{V_b} A(\vec{r}) \cdot \sum_i \frac{d}{dt} m_i(\vec{r}, t) dV \quad (1)$$

where $A(\vec{r})$ is the NMR receiving antenna spatial sensitivity function and $m_i(\vec{r}, t)$ is the nuclear magnetization of the i-th body component as a function of time and position of the elementary volume dV inside the chamber 18. The nuclear magnetization can be further presented in the form:

$$m_i(r,t) = m_{0i}(\vec{r},t) \cdot k(\vec{r}) \quad (2)$$

where $k(\vec{r})$ is a coefficient representing inhomogeneity of nuclear magnetic excitation conditions at every point in space within the chamber 18, and $m_{0i}(\vec{r},t)$ represents the magnetization that would be obtained from a perfectly uniform excitation with $k(\vec{r})=1$ within the entire chamber 18, that is, if the chamber 18 were filled with a homogeneous material, the condition $k(\vec{r})=1$ would assure that the magnetization would be spatially uniform.

The coefficient $k(\vec{r})$ depends on the spatial distribution of the RF magnetic field, the frequency spectrum of the RF magnetic field, the frequency spectrum of nuclear magnetic spins in the object being analyzed, and the RF receiver system frequency and spatial response The quantities of interest in body composition measurements are $$M_i(\vec{r}, t) = \int_{V_b} m_{0i}(\vec{r}, t) dV \quad (3)$$

where $V_b$ is the body volume. In the case of homogeneous magnetization, $m_{0i}(\vec{r},t) = \text{const}, \forall \vec{r} \in V_b$, equations (1) and (2) allow for describing the NMR signal in the form:

$$S(t) = \left[ V_b \cdot \sum_i m_{0i}(t) \right] \cdot (1/V_b) \cdot \int_{V_b} k(\vec{r}) \cdot A(\vec{r}) dV \propto \sum_i M_i(t) \quad (4)$$

Equation (4) shows that the NMR signal from a homogeneous and homogeneously magnetized body is directly proportional to the quantity of the particular material of interest. Any movement of the body may affect the total signal amplitude but it will not affect the ratio between signal components.

Homogeneous magnetization and composition is clearly not the case for inhomogeneous objects such as a living organism with naturally distributed fat and lean tissues ($m_{0i}(r,t) \neq \text{const}$). The conditions for the NMR signal to precisely represent true body composition in this case are $k(\vec{r})=\text{const}$ and $A(\vec{r})=\text{const}$ so that:

$$S(t) = \text{const} \cdot \sum_i \int_{V_b} m_{0i}(\vec{r}, t) dV \propto \sum_i M_i(t) \quad (5)$$

The example apparatus minimizes spatial variations of the coefficient k and of the antenna sensitivity function A within the sample chamber. It will be readily appreciated by those skilled in the art that similar results, as they pertain to accuracy and speed of measurement, could be obtained for body composition analysis by using NMR measurement systems and techniques known in the art. For example, well known NMR laboratory composition analysis systems have, in the centermost portions of their sample chambers, antenna sensitivity distribution and static magnetic field homogeneity such that accurate composition analysis can be made on inhomogeneous and/or moving objects over a very small volume. In fact, such systems known in the art have been used successfully to perform body composition analysis of very small laboratory mice. However, it would be impractical to increase in size the structures of such known in the art apparatus in order to perform similar whole body composition analysis on much larger animals, for example rats, dogs or even humans. Embodiments of methods and apparatus according to the invention, by contrast, provide accurate whole body composition of much larger animals but maintain practical size, cost and weight of the overall apparatus.

Figure 2A:
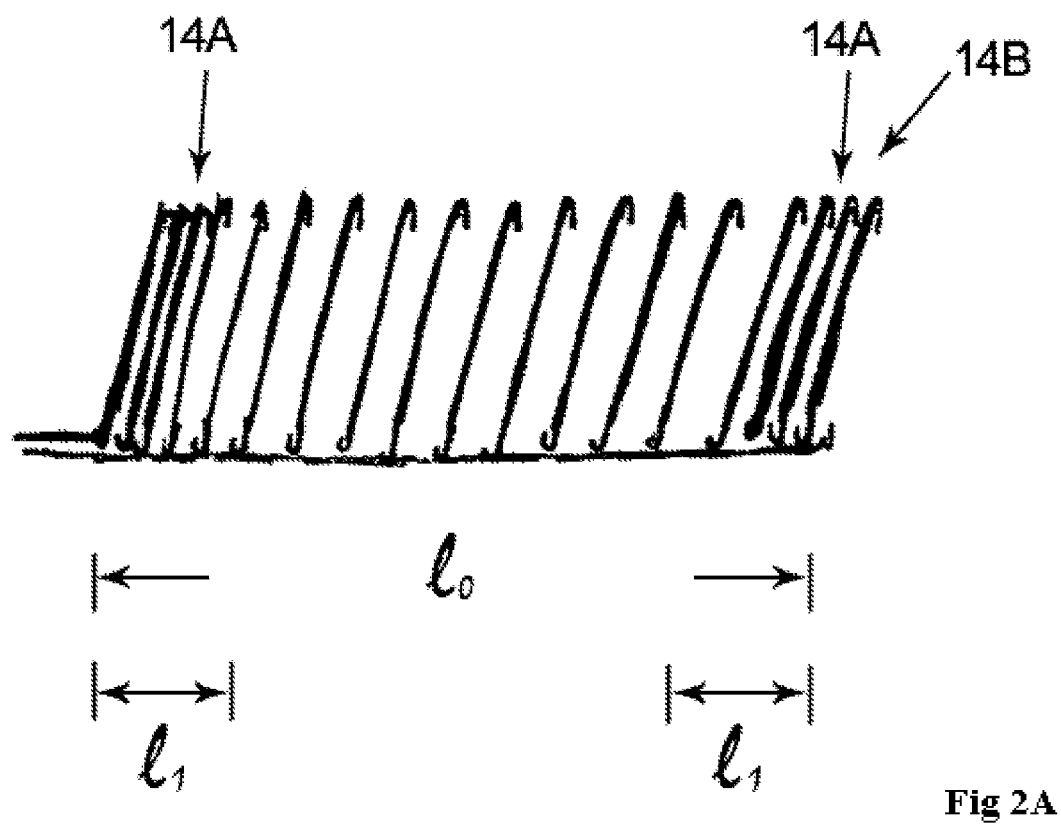
FIG. 2A shows one embodiment of an antenna for the apparatus shown in FIG. 1.

FIG. 2A shows an example of an antenna that generates an RF magnetic field having inhomogeneity of less than about 2% over the entire volume of the chamber (18 in FIG. 1). The antenna coil 14B has a total length along its longitudinal axis represented by $l_0$. Over the central portion of the antenna coil 14B, coil windings have a first "turn density" (number of turns per unit length along the coil axis). At each longitudinal end of the antenna 14B is a "booster coil", shown at 14A, each of which has a selected length along the axis represented by $l_1$, and a turn density of about twice that of the central portion. Preferably, the axial length of each of the booster coils, $l_1$, is about one-eighth the total axial length $l_0$ of the antenna 14B. It will be readily appreciated by those skilled in the art that reduced RF field inhomogeneity could be obtained by increasing the axial length of the antenna with respect to the axial length of the sample chamber. Advantageously, an antenna configured as shown in FIG. 2A and as described above provides reduced RF field inhomogeneity while maximizing the effective sample chamber length with respect to the antenna length along the respective longitudinal axes.

Figure 2B:
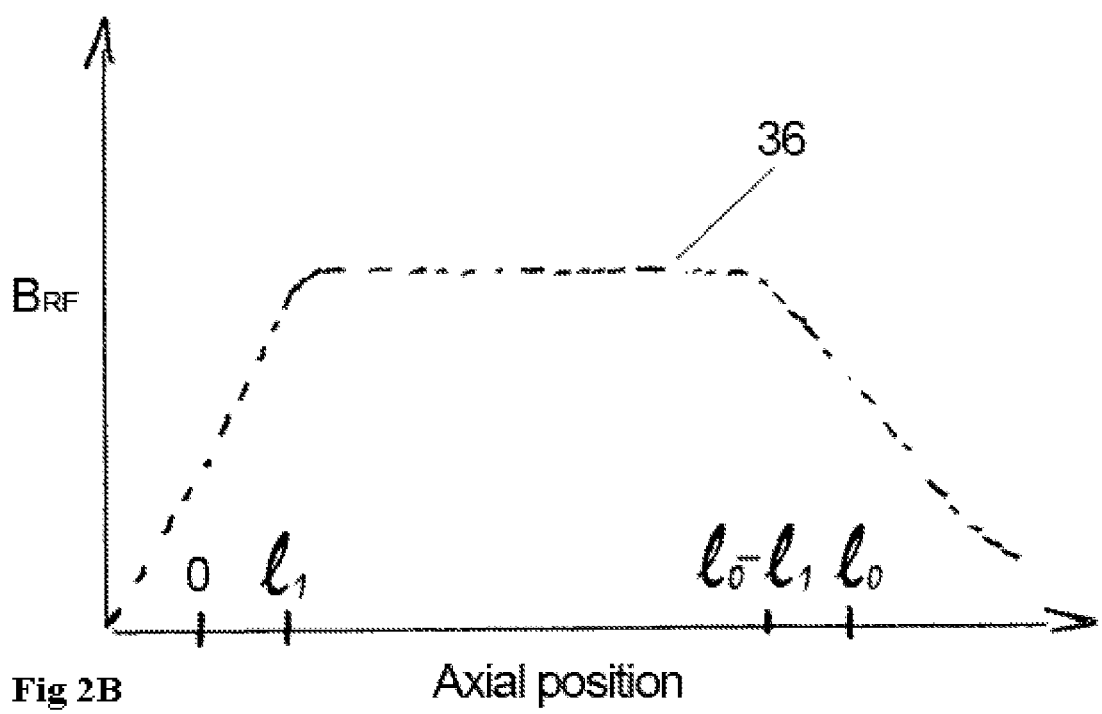
FIG. 2B shows a graph of RF magnetic field amplitude with respect to axial position along the example apparatus shown in FIG. 1.
Figure 2C:
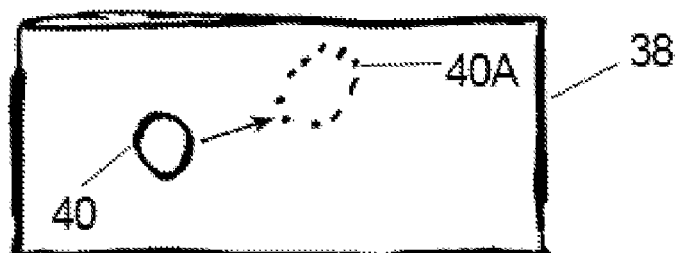
FIG. 2C illustrates possibility of movement of an object being examined by the apparatus of FIG. 1 without materially affecting measurements made by the apparatus.

The RF magnetic field distribution along the longitudinal axis of the antenna coil 14B is shown in FIG. 2B. According to the reciprocity principle, the spatial distribution of the RF magnetic field represented in FIG. 2B should be substantially the same as the spatial distribution of the antenna sensitivity function, when the same antenna is used for both RF magnetic field generation and NMR signal reception. FIG. 2C shows that a body part shown at 40 disposed within the axial limits 38 defined by the chamber (18 in FIG. 1) can move, such as shown at 40A in FIG. 2C, and still induce a substantially equal amplitude incremental NMR signal component in the antenna (14 in FIG. 2A). The body part 40 may be a portion of an entire body of an animal subject to movement within the chamber (18 in FIG. 1), or it may represent the entire animal disposed in a chamber larger than the animal itself.

Figure 3A:
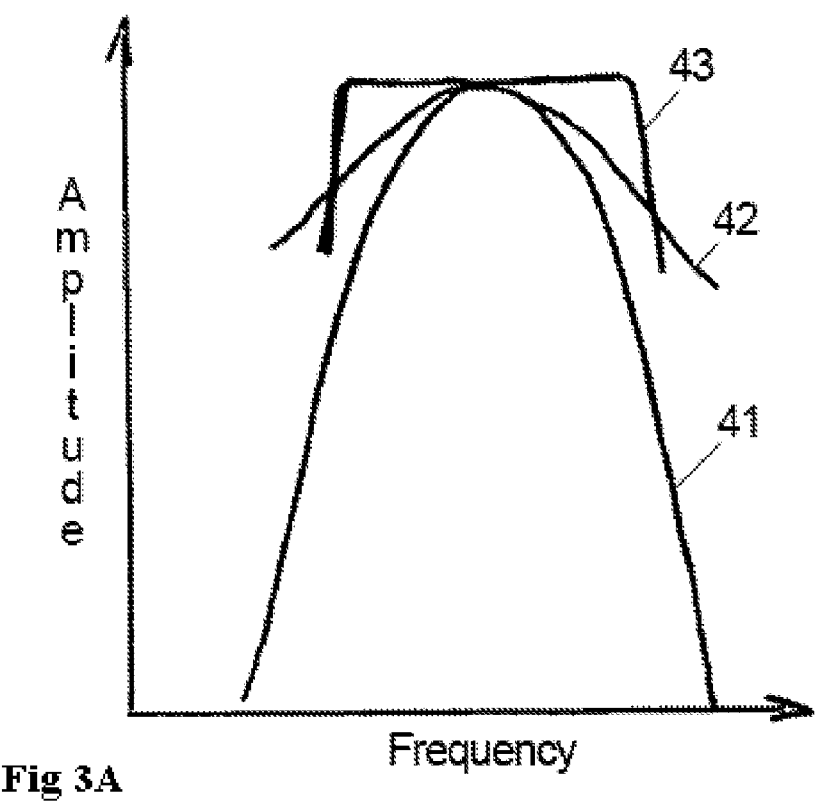
FIG. 3A is a graph of frequency content of different types RF pulses applied to the antenna of the apparatus of FIG. 1.
Figure 3B:
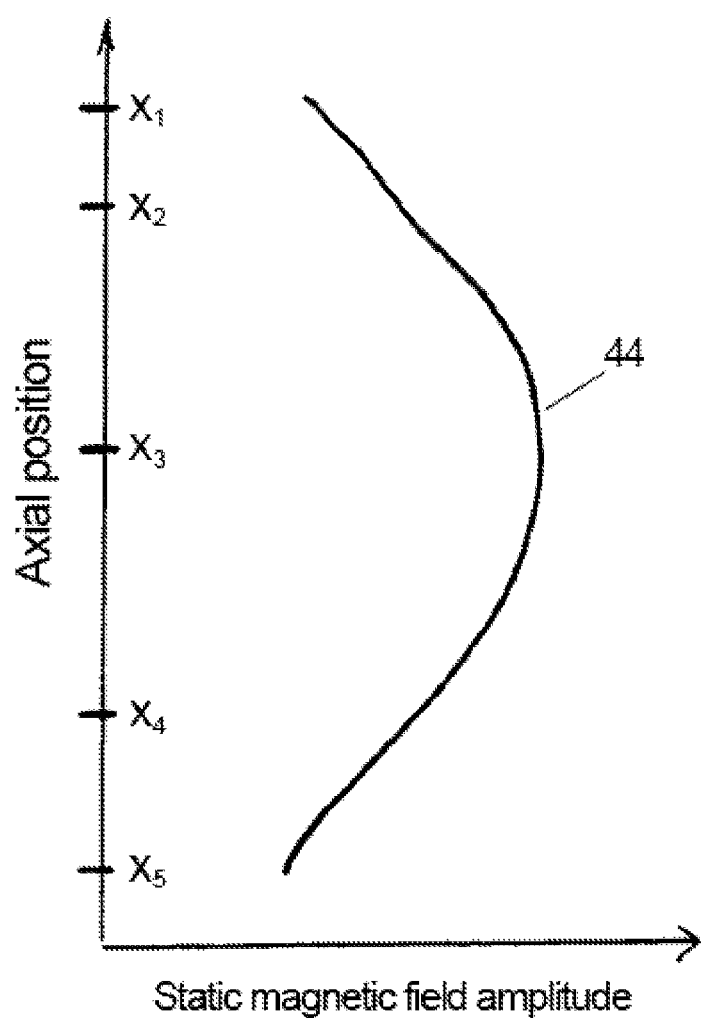
FIG. 3B is a graph of static magnetic field amplitude with respect to axial position along a sample chamber of the apparatus of FIG. 1, and corresponding magnetic resonance conditions with respect to the RF pulse frequency of FIG. 3A.
Figure 3C:
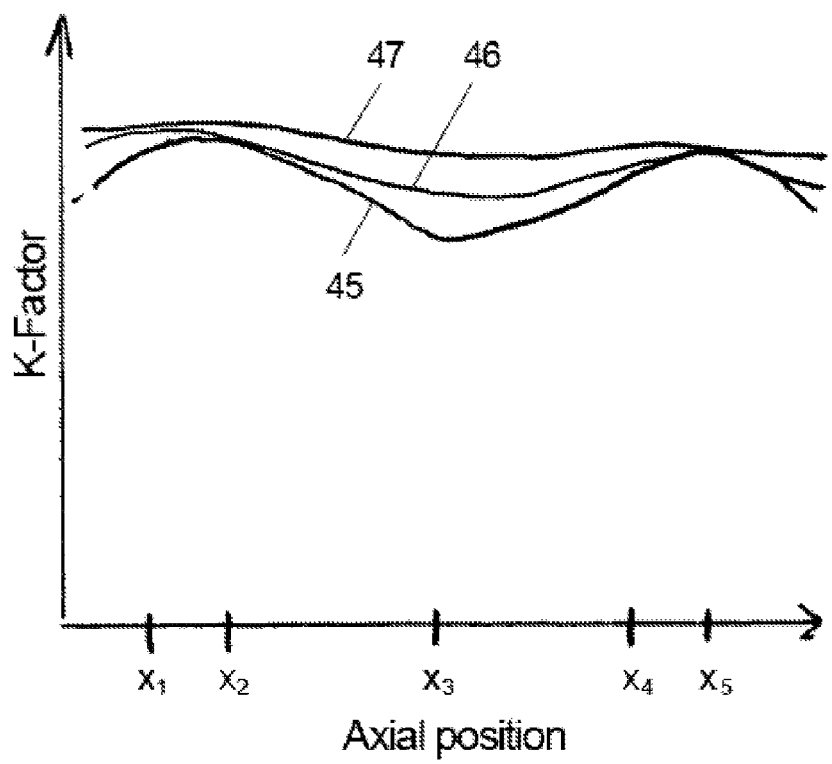
FIG. 3C is a graph of relative sensitivity of NMR measurement with respect to position within the sample chamber for various RF pulse types as shown in FIG. 2A.
Figure 3C:

The foregoing description with respect to FIGS. 2A, 2B and 2C explains an antenna structure intended to minimize spatial variation of the antenna sensitivity function A (from equation (5) above). FIGS. 3A, 3B and 3C will be discussed below with respect to the aspects of the invention related to minimizing spatial variation in the coefficient k (from equation (5) above).

FIG. 3A is a graph of amplitudes of various frequency components in RF pulses used to induce the RF magnetic field. For conventional RF pulses, shown by curve 41, the frequency spectrum of the RF magnetic field induced by these pulses transforms into spatial variation of excitation conditions, or coefficient $k(\vec{r})$ when the static magnetic field is not completely homogeneous. Variation in static magnetic field amplitude with respect to axial position is shown at curve 44 in FIG. 3B. The excitation coefficient $k(\vec{r})$ with respect to axial position x, corresponding to the static magnetic field variation (44 in FIG. 3B) and conventional RF pulse bandwidth (41 in FIG. 3A) is shown at curve 45 in FIG. 3C. Referring back to FIG. 3A, if the length of the RF pulses is shortened, the bandwidth of RF energy in the pulses is increased, as shown curve at 42. As is well known in the art, the RF pulses can be increased in amplitude in order to maintain the same amount of reorientation (same angular displacement) of the nuclear magnetic spin axes if the pulse duration is shortened. Curve 46 in FIG. 3C shows reduced variation of the coefficient $k(\vec{r})$ with respect to position when the RF magnetic field has increased bandwidth. If the increase in RF amplitude is impractical, shorter duration RF pulses at unchanged amplitude can be used, with resulting lower magnetic spin axis rotation angle. The benefit of the wider frequency bandwidth and its effect on precision of measurements outweighs some of the disadvantage of a resulting loss in NMR signal amplitude because of reduced net transverse nuclear magnetization.

Another way to optimize the RF magnetic field spectrum is the use of shaped RF pulses having an almost flat frequency spectrum. This type of frequency spectrum corresponds to a "sinc" waveform of the general form y=(sin (x)/x) in the time domain. The effect of shaped pulses is explained as applied to selective excitation in magnetic resonance imaging in, P. T. Callaghan, *Principles of Nuclear Magnetic Resonance Microscopy*, Clarendon Press, Oxford, 1991. Curve 43 in FIG. 3A shows an example bandwidth of shaped RF pulses. Curve 47 in FIG. 3C shows very little variation in excitation with respect to position when shaped pulses are used.

Yet another way to optimize the RF magnetic field spectrum is the use of composite RF pulses, a variety of which are explained in R. R. Ernst, et al., *Principles of Nuclear Magnetic Resonance in One and Two Dimensions*, Clarendon Press, Oxford, 1987. In the case of composite pulses a regular excitation or refocusing pulse is replaced by a sequence of two, three or more pulses, each of which is characterized by its own rotation angle and phase of the RF carrier. Nuclear magnetization generated using composite pulses is much less sensitive to variations in the RF magnetic field strength, and is less sensitive to static magnetic field inhomogeneity. The expression below is an example of a refocusing composite pulse (having a nominal rotation angle of 180°) containing three sub-pulses:

$$(\beta)_{\pi/2}(2\beta)_0(\beta)_{\pi/2} \qquad (6)$$

where β is the nominal rotation angle of the excitation pulse (usually 90°); and the subscripts represent the phase of the carrier frequency in the sub-pulses.

Irrespective of the type of RF pulse spectrum optimization that is used, the frequency content of the RF pulses should be selected such that even with inhomogeneity in the static magnetic field, substantially uniform nuclear magnetization occurs within any object placed in the chamber (18 in FIG. 1).

FIG. 3C illustrates the fact that in a linear approximation the coefficient $k(\vec{r})$ (or nuclear magnetization of a homogeneous object that fills all space within the object compartment) is substantially determined by the Fourier transform, or spectrum, of the RF pulse. The statement that uniform spectral density of RF pulse causes substantially uniform magnetization holds approximately true for the non-linear (typical) case as well. It is clear from FIGS. 3A, 3B and 3C that better uniformity of the static magnetic field will also improve uniformity of the nuclear magnetization. It is to be noted, though, that merely attempting to improve the uniformity of the static magnetic field requires a dramatic increase in the size, weight and cost of the magnet, irrespective of the type of magnet being used. In the invention, therefore, optimizing the RF magnetic field properties and the spatial distribution of the antenna sensitivity can facilitate the use of substantially smaller and less expensive magnets while still providing high accuracy and precision in NMR relaxometry measurements.

Rotation angle in the interval between 90 and 180 degrees for the refocusing RF pulses is also beneficial from the point of view of saving power when a large object is under investigation. In the case of measurements performed on humans, the reduced power produces less heating and therefore is advantageous from a safety point of view.

In the description above it is assumed that the receiver channel (including antenna 14, switch 20, preamp 28 and receiver 30) has sufficient bandwidth in order to uniformly (uniform signal amplitude with respect to frequency) receive signals from parts of the object (not shown) corresponding to different resonance frequencies of nuclear magnetic spins. Alternatively, the receiver channel can have a frequency response that compensates for non-uniform excitation due to inhomogeneity in the static magnetic field and the limited, non-uniform spectrum of the RF pulses.

An important relationship exists between the size of the object or body to be analyzed (related to the sample chamber volume), and the choice of NMR operating frequency (the frequency of the RF pulses applied to the antenna). As is well known in the art, the NMR frequency is proportional to the static magnetic field intensity and the gyromagnetic ratio of the nuclei being analyzed. The noise varies with the size of the antenna more slowly than the volume of substantially homogeneous irradiation.

Figure 4:
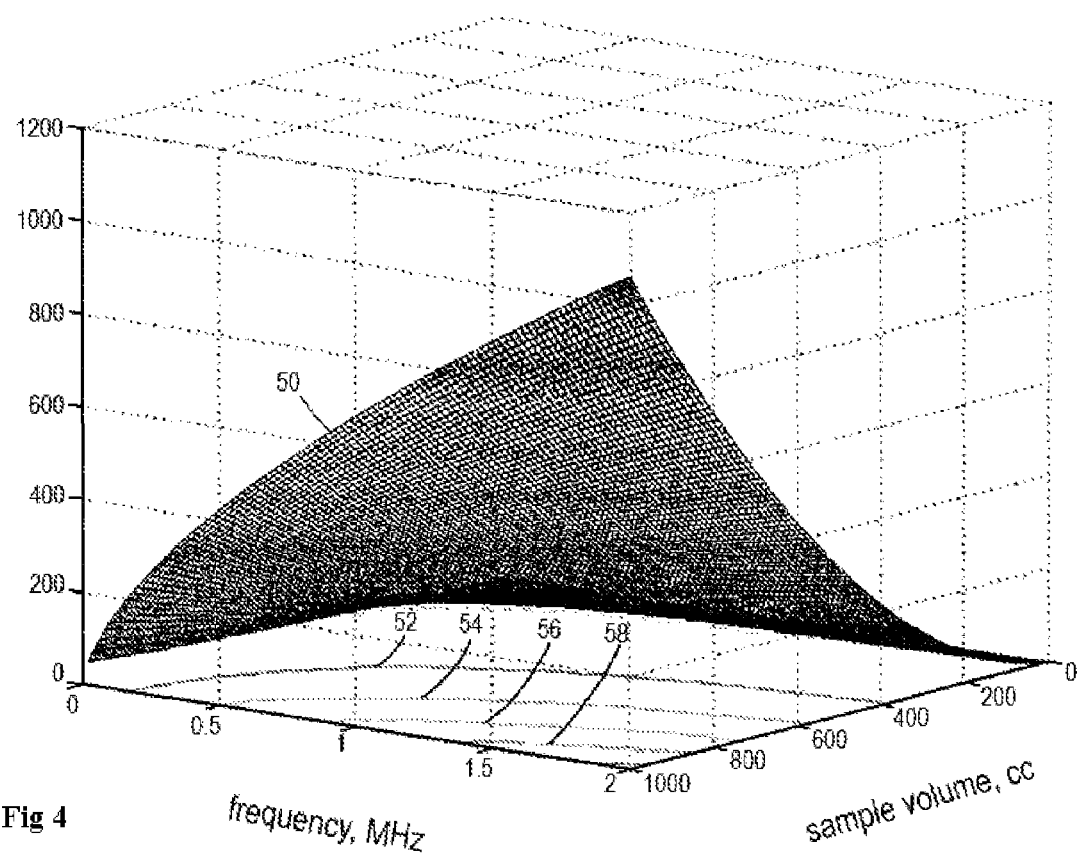
FIG. 4 is a graph of signal to noise with respect to sample chamber volume and static magnetic field amplitude.

Therefore, the same signal-to-noise ratio (SNR) can be achieved with a lower radio frequency, and therefore smaller RF power, for larger antennas and respective homogeneity volumes. FIG. 4 shows a three-dimensional graph, at surface 50, of the signal-to-noise ratio (SNR) with respect to the sample (object or body) volume and the NMR operating frequency. For a particular value of SNR, as required to perform selected duration and yet accurate NMR measurements, there is a relationship between the minimum NMR frequency that facilitates obtaining the required accuracy with respect to the volume of the sample chamber (18 in FIG. 1) where the object is placed.

The relationship for selected values of SNR is shown by curves 52, 54, 56 and 58 in FIG. 4. Curve 54, for example, represents the minimum NMR frequency as it relates to the selected chamber volume for SNR of 100. As will be appreciated by those skilled in the art, longer duration NMR measurement sequences may be used with lower SNR. The value of SNR selected will thus be related to the speed with which NMR analysis needs to be performed on any particular type of object. Irrespective of the SNR selected, the relationship between chamber volume and minimum NMR frequency can be used in various embodiments to minimize, for any selected chamber volume, the strength of the magnet used to induce the static magnetic field, while preserving acceptable accuracy and precision of measurements. Designing NMR system with minimum NMR frequency thus gives benefits of reducing the size, weight and cost of the magnet assembly for any particular sample chamber volume.

All of the foregoing attributes of an apparatus are used to maximize the volume of objects being compositionally analyzed with respect to the physical dimensions (and thus the associated cost) of the apparatus itself. The apparatus can therefore be described in general terms as having a spatial distribution of the static magnetic field and of the radio frequency magnetic field selected to minimize a penalty function, wherein the penalty function includes as variables the required measurement precision and at least one parameter related to the financial cost of the apparatus. This is in contrast to magnetic resonance imaging apparatus known in the art which must be much larger in size (and thus associated cost) to make measurements of a selected accuracy on larger and larger objects.

The foregoing apparatus, however, is only one example of apparatus that may be used with composition analysis techniques according to the invention. Generally speaking, apparatus that may be used for body composition analysis according to the invention only need to be able to make measurements that include signal components related to the longitudinal and/or transverse relaxation time of the various constituents of the body being analyzed. Further, other apparatus usable with methods according to the invention may include various devices to localize the measurements within a particular portion or portions of the entire body, rather than analyzing the entire body within the chamber as the example apparatus in FIG. 1. One example of such apparatus will be explained below with reference to FIGS. 11 through 13.

2. Analysis of Body Composition Using NMR Measurements

In one embodiment of a method according to the invention, and using an apparatus as explained above with respect to FIG. 1, a live, conscious animal (depending on the size of the apparatus, this may be a human infant or adult) is placed in the sample chamber (18 in FIG. 1). The magnet (12 in FIG. 1) induces a static magnetic field in the animal. RF pulses according to a programmed sequence are passed through the antenna (14 in FIG. 1), between which pulses, NMR signals are detected by the antenna (14 in FIG. 1). A record is made of the NMR signals thus detected, and from the detected NMR signals, composition of the animal body is analyzed. In one embodiment, the RF pulses passed through the antenna have duration, amplitude, phase, and spacing between successive RF pulses to form the well known Carr-Purcell-Meiboom-Gill (CPMG) sequence. The signals detected using a pulse sequence constitute nuclear magnetic spin echoes. Body composition may then be determined from the properties of the spin echoes in particular arrangements of sequences as will be explained further below.

Figure 5:
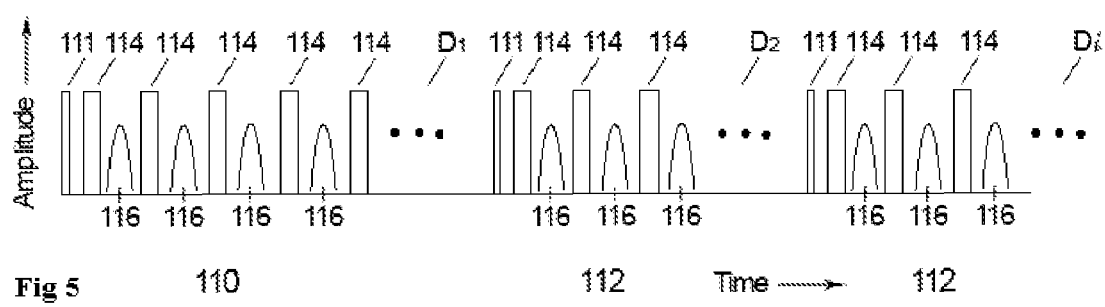
FIG. 5 shows a sequence of RF pulses and spin echo signals representing an embodiment NMR measurement technique of the present invention.

NMR data suitable for body composition analysis according to the invention are obtained from a suitable arrangement of measurement sequences. An example of such an arrangement is illustrated graphically in FIG. 5. The measurement arrangement shown in FIG. 5 is a sequence of pulses composed of a plurality of CPMG sequences. The first CPMG sequence 110 is relatively long, followed by a plurality of relatively shorter length CPMG sequences 112. Each CPMG sequence, both long and short, includes an initial transverse magnetic polarization pulse, at 111, followed by a selected number of inverting or refocusing pulses at 114. "Long" and "short" as used herein with respect to the CPMG sequences in the measurement arrangement relate to the number of refocusing pulses 114 used in the various CPMG sequences. The RF pulses passed through the antenna (14 in FIG. 1), represented by the envelopes of the pulses, are shown in FIG. 5 generally at 114. The spin echoes detected in the CPMG sequences are shown generally by their amplitude envelopes at 116. The spin echoes 116 are measured and recorded, as previously explained above with respect to FIG. 1.

Each CPMG sequence generates NMR spin echo data that can be used to determine transverse nuclear magnetic relaxation properties, such as the $T_2$ relaxation time. Recovery times $D_1, D_2, \ldots D_i$, between successive CPMG sequences are selected to be comparable to the longitudinal magnetic spin recovery time of the constituents of the body, so that the relative amplitudes of the spin echoes detected in each of the sequences can be used to determine longitudinal nuclear magnetic relaxation properties. Thus, the example CPMG sequence arrangement shown in FIG. 5 provides spin echo data that can be used to determine both transverse and longitudinal relaxation nuclear magnetic properties of the body (or body part) being analyzed.

It has been determined experimentally that NMR measurements having identifiable transverse and longitudinal relaxation components can improve the analysis of constituent composition of a body or body part as compared to using either transverse or longitudinal relaxation components alone. The overall transverse and longitudinal relaxation properties of the body (or body part) being analyzed, as reflected in the spin echoes measured as explained above, will reflect the respective masses of, and the relaxation properties of, certain constituents of the body being analyzed. In methods according to the invention, the mass (or fractional amount) of each of a selected number of constituents can be determined from the spin echoes. The following is an explanation of how this is performed according to the invention.

Methods according to the various aspects of the invention determine an amount (mass or fractional amount) of one or more selected constituents (e.g. fat, lean tissue and free fluids) in a body or body part subject to NMR measurements by calculating a predetermined function with respect to the NMR measurements. The function for each constituent is determined from a standard which represents each constituent. A generalized standard for a body constituent in the present invention is a set of substances that represents substantially all possible compositional and temperature variations of the represented body constituent (e.g., fat, lean or free fluids) in a real object (live animal or human). An example of a set of substances that defines a standard for body fat can include olive oil, canola oil and sunflower oil in various proportions and at different temperatures. The temperatures are typically in the range of about 30-40° C. A lean tissue standard may include chicken breast muscle tissue at different temperatures, as well as synthetic porous media. One example of such synthetic porous media includes substances (gels) sold under the trade name SEPHADEX G-15 or SEPHADEX G-25, by Pfizer, Inc., New York, N.Y. These substances model water in biological tissues.

It has been determined through laboratory experiments that for a given NMR measurement set (presented in the detailed description of the embodiments of the present invention) the measured NMR signals (measurement vectors) obtained on the standards corresponding to different constituents substantially do not overlap. This is a prerequisite for a successful differentiation between the body constituents. Ways to implement the differentiation are presented in the description which follows. An important aspect of methods according to the present invention is that a total amount of fat, irrespective of the type and/or distribution of fat in a body part, can be determined by applying NMR measurements of the body part to a predetermined function. The predetermined function represents calibration measurements made on a set of test substances, such as the aforementioned canola, olive and/or sunflower oils made at various temperatures. Thus, methods according to the invention enable determining total fat amount or mass within the body part without the need to compositionally analyze the various fat types within the body part or within other body parts to be analyzed. As a result, methods according to the invention enable rapid, in-vivo fat mass or content determination without the need for difficult and expensive compositional analysis.

The spin echo data from the NMR measurements made as explained above are used to construct a "measurement vector" whose components are calculated from the spin echoes. In one embodiment, each spin echo contributes to a single component of the measurement vector. For example, the component can be a convolution of the echo and a kernel. The kernel can be selected to represent a specific purpose, such as yielding an overall amplitude of the echo by averaging several measured values in the middle of interval 116.

In one embodiment, the predetermined function is linear and its calculation is calculation of a scalar product of a measurement vector and a regression vector, namely, given a measurement vector V, the masses of a predetermined set of body constituents are obtained as follows. Based on pre-arranged calibration measurements, as will be further explained below, each constituent A has associated with it a regression vector $R_A$, of the same dimension as the measurement vector V. The mass of constituent A in the body or body part being analyzed is proportional to, or, in a simple version can be assumed to be equal to the scalar product $V \cdot R_A$ The set of regression vectors $\{R_A\}$ for a set of constituents $\{A\}$ is determined from a set of calibration measurement vectors. The calibration measurement vectors are obtained in an "a priori" calibration measurement procedure, wherein each regression vector $R_A$ depends on the selection of constituents in $\{A\}$. $R_A$ cannot be determined without the whole set of constituents $\{A\}$ being defined first.

In some embodiments, the regression vectors $\{R_A\}$ are obtained from some variant of least squares (LS) fitting of calibration vectors. The dimension of a regression vector is usually larger than the number of calibration vectors, and therefore the LS fitting must be preceded by a dimension reduction procedure. In one embodiment, which will be further explained later in this description, the dimension reduction procedure takes the form of restricting the regression vector to a subspace formed by the calibration measurement vectors. In another embodiment, which will be further explained later in this description, the regression vector is further restricted to a sub-subspace of the calibration measurement vector subspace by means of a principal component analysis (PCA).

In some embodiments, calibration vectors are smoothed in the following sense. The plurality of components of a calibration measurement vector in which a single component corresponds to one CPMG spin echo is regarded as a "regression function" of the consecutive number of the echo. This function is approximated by a piece-wise smooth function, such as, in one example, a sum of exponents with non-negative coefficients.

Figure 6A:
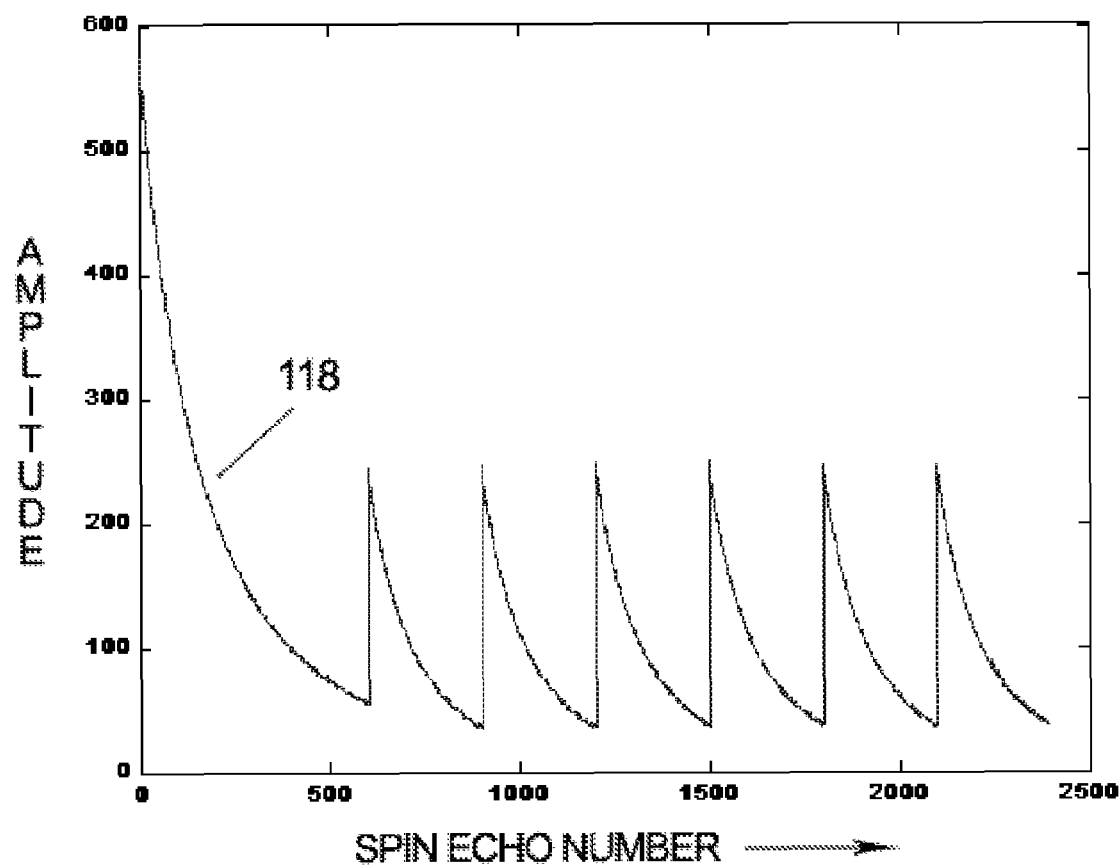
FIGS. 6A, 6B and 6C represent vectors of measurement data corresponding to three major component of the body: fat, lean and free fluids respectively.
Figure 6B:
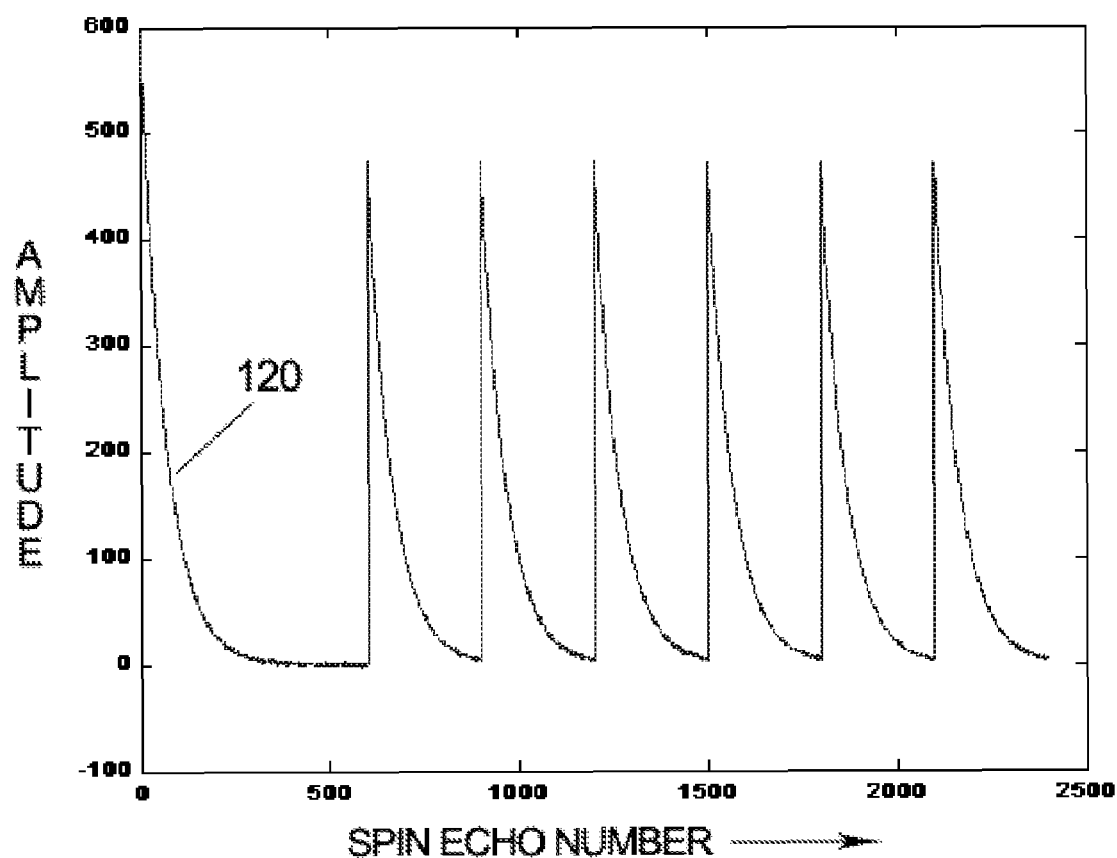
Figure 6C:
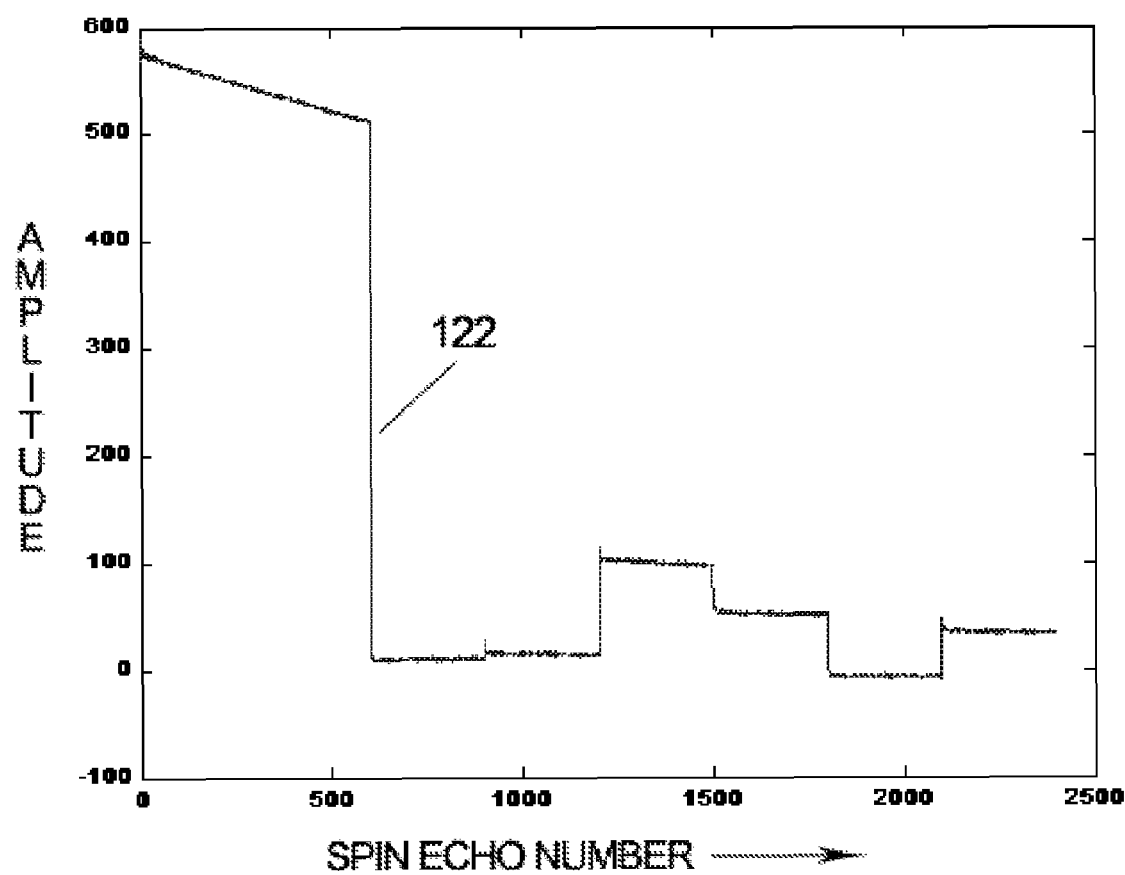
Figure 6D:
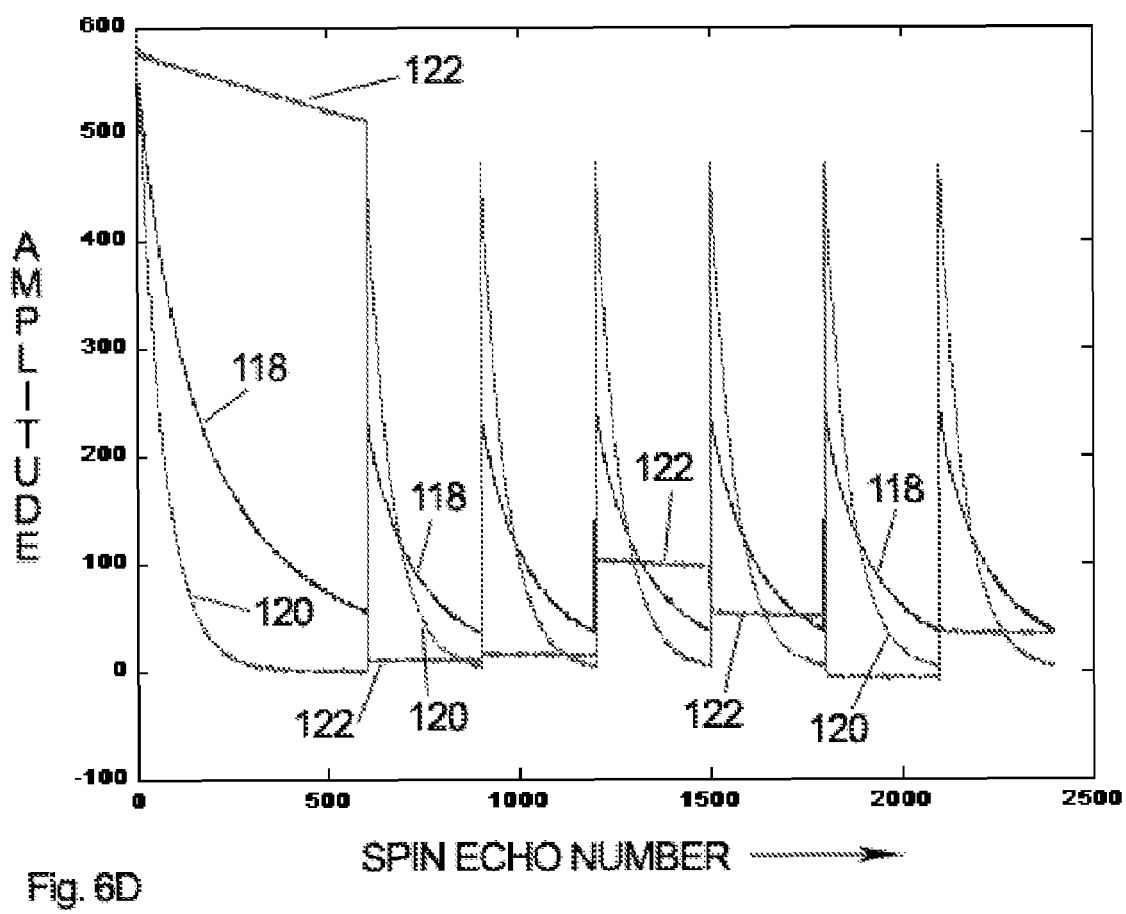
FIG. 6D shows the graphs of FIGS. 6A, 6B and 6C superimposed on a single graph.

In one embodiment, the calibration set of measurement vectors comprises NMR spin echo measurements, made using the long and short duration CPMG sequences as explained above with respect to FIG. 5, corresponding to each of three selected major constituents of the body. The three selected body constituents in this example are fat tissue, lean tissue, and free fluids. The calibration measurement vectors may be averaged over a few separate sets of NMR calibration measurements made on each calibration sample to reduce the effects of noise in the calibration measurements. FIGS. 6A, 6B and 6C represent spin echo amplitude measurements, at curves 118, 120 and 122, respectively, made using the measurement arrangement shown in FIG. 5.

It has been determined experimentally that the NMR spin echo amplitude response of real constituents of the bodies of animals, such as mice and rats, as well as humans, can be adequately characterized with respect to quantities or fractional amounts of fat tissue, lean tissue and free fluid by making calibration measurement sets using canola oil to represent the fat tissue, using chicken breast muscle tissue to represent the lean tissue, and by using 0.9 percent sodium chloride (saline) solution to represent the free body fluids. This is a particularly important finding with respect to characterization of fat tissue and lean tissue because of the compositional variations of such tissues within a living body.

In one embodiment, which we designate "single-sample", the spin echo amplitudes of FIGS. 6A, 6B and 6C are then used to create three calibration measurement vectors $V_{fat}$, $V_{lean}$ and $V_{saline}$, for fat tissue, lean tissue and free body fluids, respectively. In this embodiment, the following expressions are used to determine the regression vectors based on $V_{fat}$, $V_{lean}$ and $V_{saline}$ that were normalized to 1 gram of mass, and averaged over several samples of each substance:

$$R_{fat} = V_{lean} \times V_{saline} [V_{fat} \cdot (V_{lean} \times V_{saline})]^{-1}, \quad (7)$$

$$R_{lean} = V_{saline} \times V_{fat} [V_{fat} \cdot (V_{lean} \times V_{saline})]^{-1}, \quad (8)$$

$$R_{saline} = V_{fat} \times V_{lean} [V_{fat} \cdot (V_{lean} \times V_{saline})]^{-1}, \quad (9)$$

where the cross-product is defined as a usual three-dimensional cross product in the three-dimensional linear sub-space, extended over the three calibration measurement vectors, $V_{saline}$, $V_{lean}$, and $V_{fat}$.

In other embodiments, which are designated "multi-sample", in order to improve the accuracy of the results of the analysis, the set of calibration measurements used to generate the regression vectors for any one or more of the constituents can include making calibration measurements on more than one sample of a particular constituent. For example, measurements made on the same physical sample of a constituent may be made at different temperatures. Another variation includes making calibration measurements on different samples of the same substance representing the same body constituent, for example, different types of oil, or different samples of animal lean muscle tissue. The use of multi-sample calibration measurements sets reduces composition analysis error due to factors such as natural variations in the chemical composition of a particular body constituent, or variation in the body temperature, each of which may result in slightly different NMR relaxation properties for the same constituent.

In "multi-sample" embodiments where the regression vectors are calculated from measurements made on multiple samples and/or measurements made at multiple temperatures, there will be several calibration measurement vectors for each basic substance (constituent). The respective sets of vectors are denoted as $V_s = \{V_{saline,\ i}; i=1, \ldots, N_s\}$, $V_1 = \{V_{lean,\ i}; i=1, \ldots, N_1\}$, and $V_{fat} = \{V_{fat,\ i}; i=1, \ldots, N_f\}$, where $N_s$ represents the total number of free fluid calibration measurement vectors, $N_1$ represents the total number of lean tissue calibration measurement vectors, and $N_f$ represents the total number of fat tissue calibration measurement vectors. The complete set of calibration measurement vectors $V_{all} = \{V_s, V_1, V_f\}$ contains the total of $N_{all} = N_s + N_1 + N_f$ calibration measurement vectors.

The canola oil and saline solution samples, used to produce calibration vectors for fat and free fluids, respectively, can be well standardized with respect to chemical composition. Therefore, differences in NMR response for various samples of canola oil and saline solution will more closely reflect differences such as temperatures rather than differences in chemical composition. On the other hand, at the present time, a method for creating a stable (compositionally uniform) laboratory standard for the chicken breast muscle tissue to represent lean body tissue (or other substance used to represent lean body tissue) is not yet established. As a result, different samples of chicken breast tissue may noticeably differ in chemical composition. The differences in the NMR signal response caused by differences in composition and by different constituent temperatures are of comparable magnitudes for various samples of chicken breast tissue. In one example, to reduce errors in body composition analysis, more than 100 different samples of chicken breast muscle tissue were used to generate the set of calibration measurement vectors for lean tissue, $V_1$.

In one "multi-sample" embodiment, the principal component analysis (PCA) is applied to the set of calibration measurement vectors, $V_{all}$, in the following form. An arbitrary orthonormal basis $B = \{B_j, j=1, \ldots, D\}$ is formed for the sub-space stretched on the full set of the calibration vectors, where $B_j$ are the vectors of the basis, and its dimension is $D \leq N_{all}$. Then, each calibration measurement vector $V_i$ (from the set $V_{all}$) is represented by a row of its coordinates $U_i = \{U_{i1}, U_{i2}, \ldots\}$ in basis B so that $$V_i = \Sigma_j U_{ij} B_j. \quad (10)$$

These coordinates are used to construct a covariance matrix of the calibration measurement vectors according to the expression:

$$M_v = \Sigma_i U_i^T U_i, \quad (11)$$

The eigenvalues $e_i$, $i=1, \ldots, D$ and eigenvectors $E_i$, $i=1, \ldots, D$ of the covariance matrix $M_v$ are then determined. Next, the principal component analysis (PCA) invokes some principles, criteria or rules by which a part of the eigenvectors are selected to form the basis of a subspace on which further processing (such as least squares fitting) is performed. In one embodiment, a fixed small number of eigenvectors having the largest eigenvalues is selected. In another embodiment, the eigenvectors are selected from the comparison of their respective eigenvalues with eigenvalues that would be found if the calibration measurement vectors were replaced by pure noise measurement vectors obtained without actual samples placed in the measurement apparatus. In yet another embodiment, the principal component selection procedure can include analysis of variability of regression vectors as a function of the number of eigenvectors with the largest eigenvalues selected. The variability of a regression vector can be associated, for instance, with the norms of the derivatives of the regression functions defines above. In yet another embodiment, the principal component selection procedure can involve examination of errors of predicting constituent masses for a test set of measurements vectors as functions of the number of eigenvectors with the largest eigenvalues selected. In yet another embodiment, the principal component selection procedure can include analysis of the fractions of test measurement vectors obtained from target bodies, such as animals, which reside within the sub-space extended onto the eigenvectors selected as a function of the number of the largest eigenvalues selected. Some of these embodiments are explained in further detail below.

After the PCA, having selected the set of some $N_e$ eigenvectors to be further used, a partial subspace, $S_p$ is formed, of dimension $N_e$, stretched on these eigenvectors.

Next, for each of the calibration measurement vectors in the $V_{all}$ calibration measurement set, its projection P, onto the subspace $S_p$ is determined. These projections, $\{P_i, i=1, \ldots, N_{all}\}$ are then used for subsequent partial least squares fitting, as follows. Let $A_i$ represent the mass of substance A in measurement i, then, using all coordinates with respect to the basis of the selected partial subspace, a linear system of equations is obtained:

$$A_i = P_i \cdot R_b^A, \; i=1, \ldots, N_{all} \tag{12}$$

where $R_b^A$ are the unknown and sought-after components of the substance A regression vector with respect to the basis, $E_i, i=1, \ldots, N_e$, of the partial subspace. The foregoing procedure of constructing the basis of the partial subspace assures that the number of eigenvectors is not larger than the number of vectors in the calibration measurement set ($N_e \leq N_{all}$) so that the system of linear equations is either fully determined or over-determined. The system of linear equations can therefore be solved by a least squares fitting method, for example, as follows.

Let A represent a column of length $N_{all}$ composed of the masses of substance A present in the $N_{all}$ measurements, and let $P_{all}$ represent the matrix of $N_{all}$ rows, each of length $N_e$, formed by the $N_{all}$ vectors $P_i$. Then:

$$R_b^A = (P_{all}^T P_{all})^{-1} P_{all}^T A. \tag{13}$$

The components of the regression vector in the original basis are:

$$R_A = E^T R_b^A, \tag{14}$$

where matrix E is formed by the rows made of the components of the partial subspace basis vectors.

In some "multi-sample" embodiments, one or more of the constituents have calibration measurement vectors obtained at more then one temperature. For such a constituent of a body, an evaluation of its temperature distribution can be made as follows. Instead of using a single regression vector for this constituent, separate regression vectors are calculated for each temperature of this constituent and these regression vectors are used to determine separately the masses of portions of this constituent at these temperatures in the body. The errors in the derived temperature distribution properties are smaller for constituents whose NMR properties change more widely with temperature. In particular, the fat tissue is most sensitive to temperature variations, so that, for instance, the canola oil equivalent temperature distribution can be better determined than that of lean tissue or water.

Figure 7:
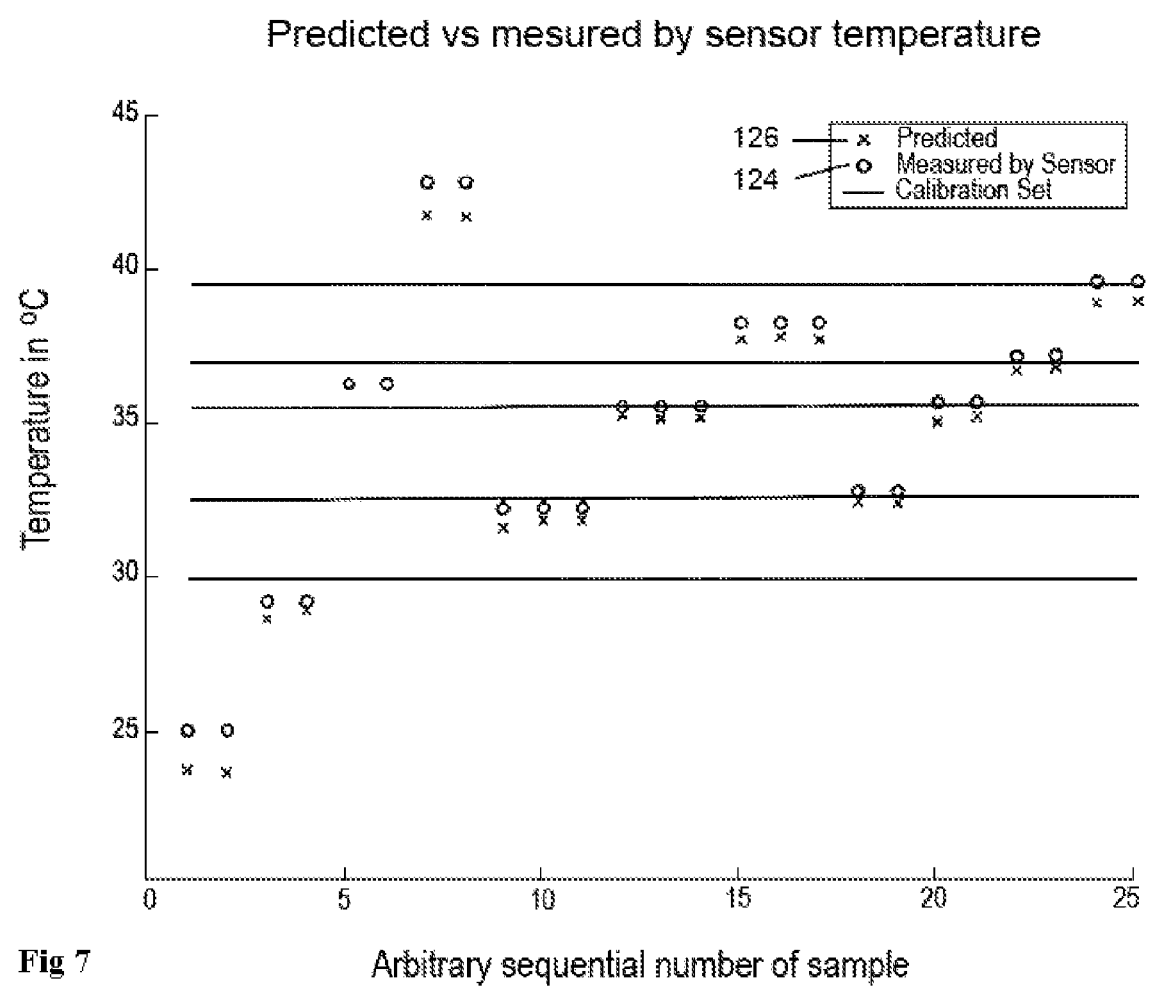
FIG. 7 illustrates results of body fat temperature assessment based on a calibration set that includes fat measured at different temperatures.

The results presented in FIG. 7 illustrate determination of temperature of fat using the technique described above, in comparison with temperature sensor data. The calibration measurement set used for the data presented in FIG. 7 includes measurements made on four samples of chicken breast meat, measurements made on two samples of saline solution, and measurements made on two samples of canola oil, each made at five different temperatures. The five calibration measurement temperatures are shown at 124. The testing was made on twenty five measurement vectors obtained from samples of canola oil held at eleven different temperatures, some of the testing temperatures outside the range of the five calibration temperatures, and some inside this range. The temperatures measured by sensors are shown at 125, and the temperatures predicted using the technique described above are shown at 126.

Figure 8:
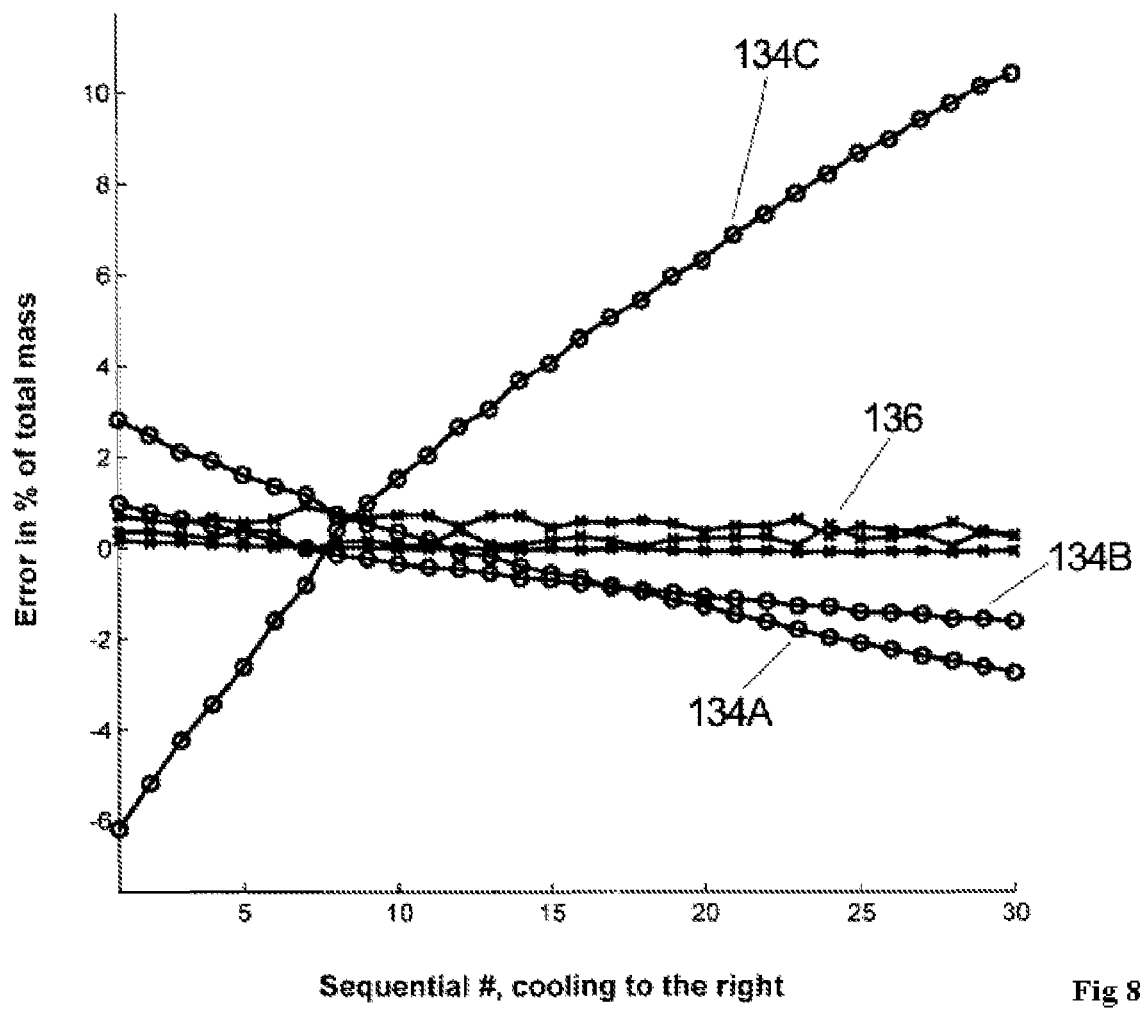
FIG. 8 illustrates using a multi-sample calibration measurement set to reduce analysis error due to constituent temperature variation.

In some embodiments, the use of multi-temperature calibration measurements sets helps to reduce temperature-dependent errors in the determined constituent masses even when the details of the temperature distribution are not included in the body composition analysis requirements. FIG. 8 shows the evolution of errors in estimating the masses of fat, lean, and saline in a cooling test sample. Each sequential measurement indicated on the ordinate axis of the graph in FIG. 8 corresponds to a lower temperature of the sample which was initially heated to about 38 degrees C. and was then allowed to cool to nearly the room temperature (that is the temperature decreases from left to right). Dotted lines 134A, 134B and 134C represent errors corresponding to single-temperature calibration, while solid lines 136 represent multi-temperature calibration. As can be inferred from FIG. 8, using multiple samples of each constituent in the calibration measurement set at a plurality of temperatures reduces the analysis error where the sample is subject to variable or unknown temperatures.

Figure 9:
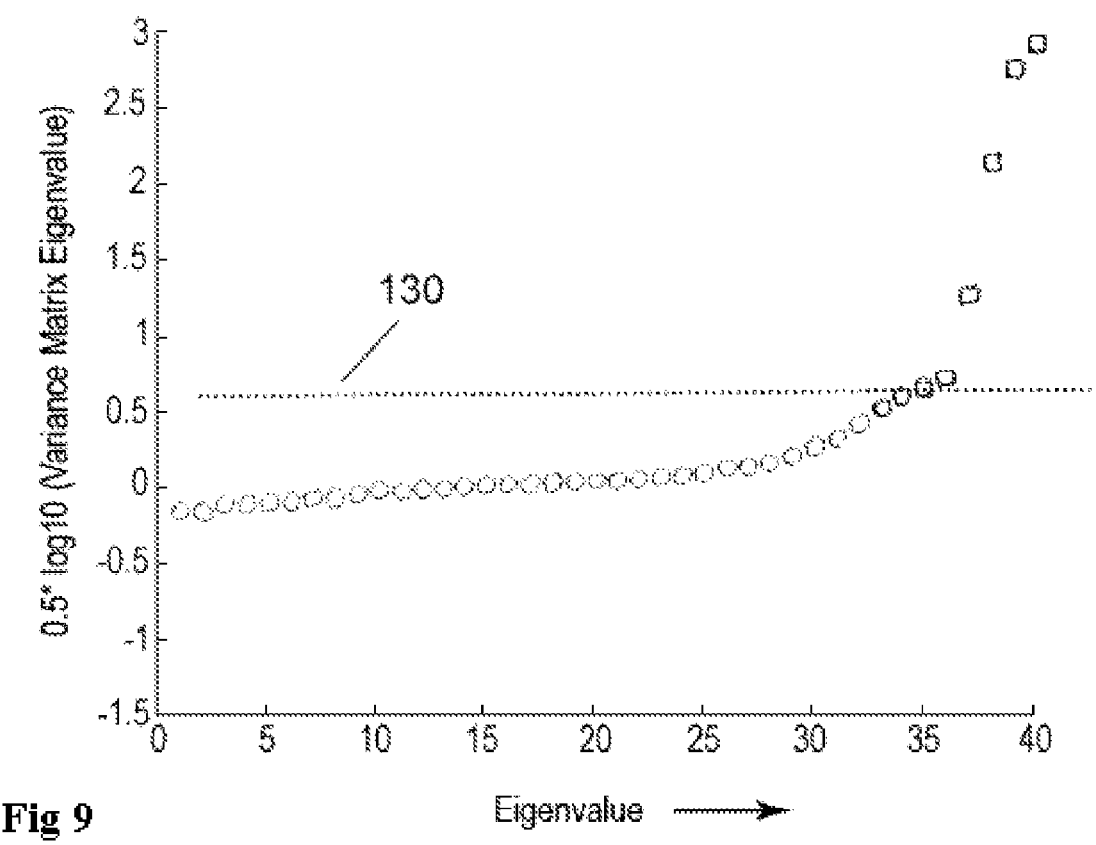
FIG. 9 illustrates choosing the set of significant principal components in the calibration data based on a comparison of eigenvalues of a covariance matrix with eigenvalues obtained from measuring system noise.
Figure 10:
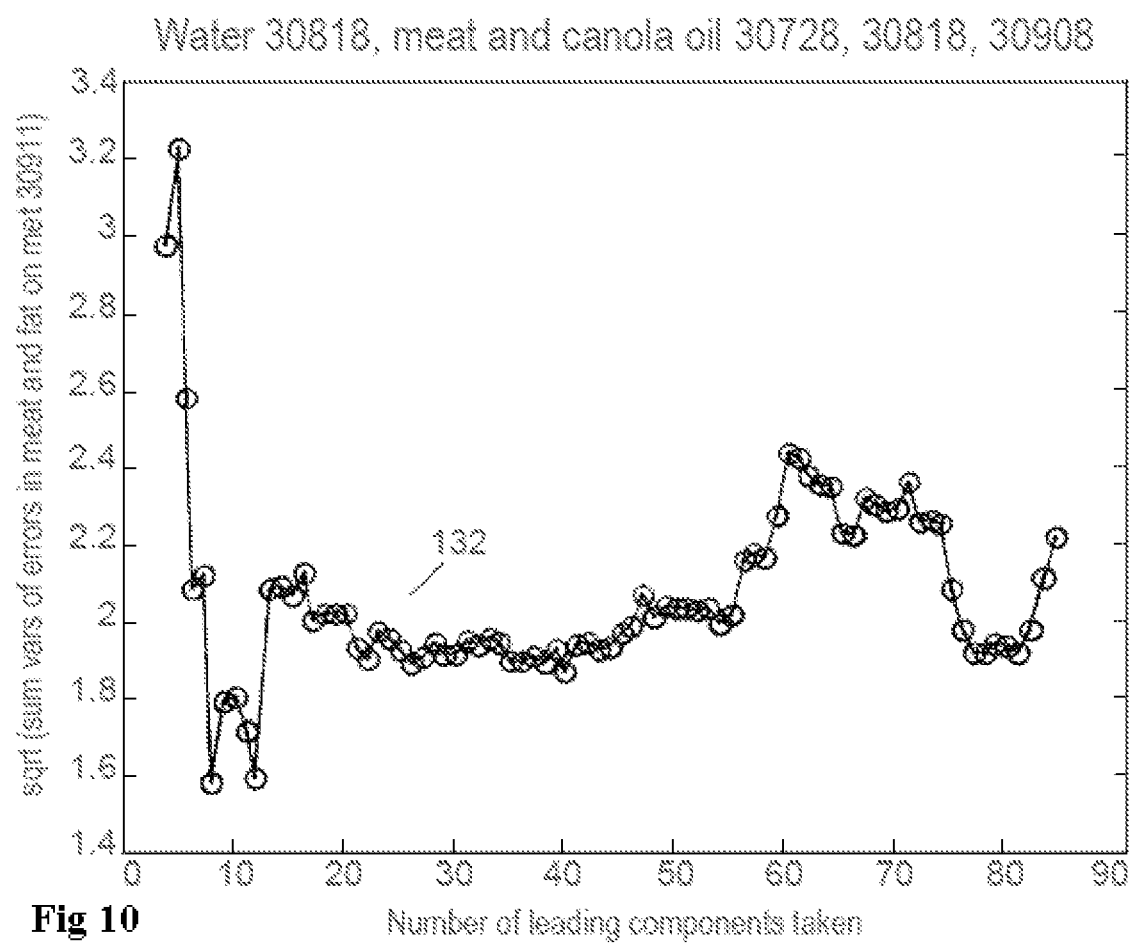
FIG. 10 illustrates criteria for choosing the set of significant principal components in the calibration data based on minimizing measurement errors.

FIGS. 9 and 10 illustrate two of the procedures described above for selecting the number, $N_e$, of eigenvectors with the largest eigenvalues, that are to be used for the partial least squares fitting to generate the regression vectors for each constituent. The graph in FIG. 9 shows the variance matrix eigenvector number on the coordinate axis and the variance matrix eigenvalues for each corresponding eigenvector on the ordinate axis. The procedure illustrated in FIG. 9 is based on a comparison of the variance matrix eigenvalues with the maximum eigenvalue of noise in the acquisition system.

Acquisition system noise eigenvalues can be determined from data acquired without a sample in the chamber (18 in FIG. 1). The noise level is shown by the dashed line 130 in FIG. 9. In one embodiment, only eigenvectors with eigenvalues exceeding the maximum eigenvalue of the acquisition system noise are taken to form the partial subspace, $S_p$.

FIG. 10 illustrates a different procedure for selecting the most significant eigenvectors. The graph in FIG. 10 shows the sum of the squares of the analysis errors for some test measurements, shown at curve 132, plotted with respect to the number of calibration sample measurement vectors used to generate the regression vector. FIG. 10 suggests that there is an optimum number of calibration measurement vectors that should be used to generate the regression vectors for the composition analysis procedure of the invention. In the embodiment illustrated in FIG. 10, determining the set of significant eigenvectors is based on the errors of mass predictions for a set of test measurements.

The procedures representing different embodiments of the present invention have as a goal better accuracy and precision in analyzing body composition in the presence of different uncertainty factors such as natural variations of NMR relaxation properties of the same substance present in the body, or uncertainty due to variations in temperature of a constituent (for example, possible variation of temperature of fat tissue depending on its location within the body being analyzed).

3. Alternative Embodiments of a Measurement Apparatus and Associated Methods

The previous embodiments of an apparatus, and methods according to the invention which use the foregoing apparatus, generally relate to analysis of body composition within a nuclear magnetic resonance volume of investigation which includes the entire body to be analyzed. It is important to recognize that methods according to the invention are not limited in scope to techniques that include measurement of an entire body for analysis of the NMR measurements made thereon. Following is a description of a different NMR measuring apparatus which may be used with other embodiments of a method according to the invention. The apparatus and methods which are described below include some form of localization of nuclear magnetic resonance measurements to within a selected portion of the body being analyzed, and subsequent composition analysis of the body portion from the nuclear magnetic resonance measurements so localized. In one exemplary technique, the described localized composition analysis is repeated in one or more additional selected body portions, and, optionally, the results obtained for the selected body portions are summarized to obtain nuclear magnetic resonance composition analysis of a larger body part or of the whole body.

Figure 11:
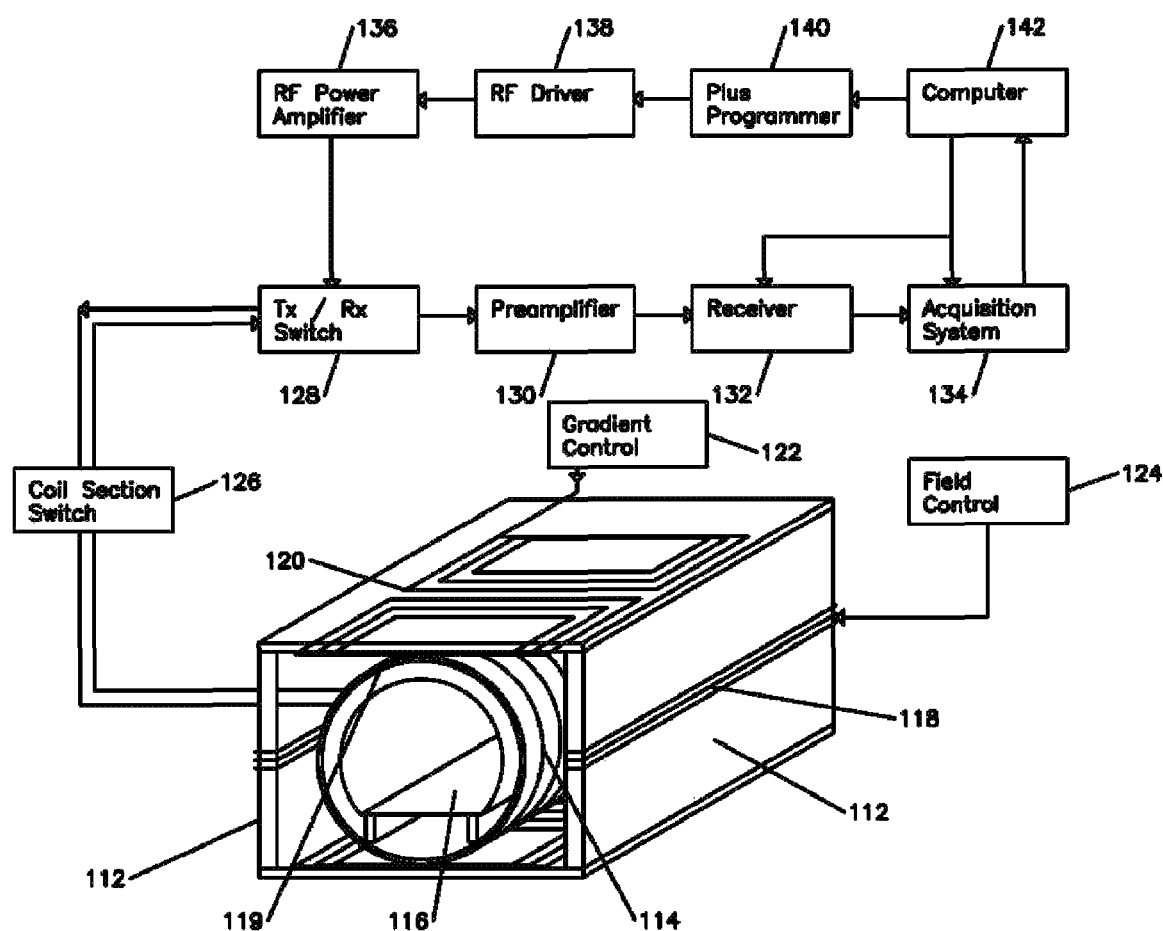
FIG. 11 shows an alternative embodiment of an apparatus including devices to localize NMR measurement within selected body portions.

One embodiment of a nuclear magnetic resonance (NMR) apparatus usable to make NMR measurements, including localization of NMR excitation and measurement within selected body parts is shown generally in FIG. 11 at 110. The apparatus 110 of FIG. 11 is similar to the apparatus of FIG. 1, but includes various devices to localize excitation and detection of NMR phenomena to within selected parts of the body, as will be explained below. The apparatus 110 includes a magnet 112 disposed around or on opposed sides of a sample chamber 116. The magnet 112 may be a permanent magnet, or an electromagnet, and is configured to induce a substantially homogeneous static magnetic field within the sample chamber 116. The sample chamber 116 may be defined by an enclosure such as a polycarbonate tube or box, shown generally at 119 in FIG. 11. The enclosure 119 may be made from any substantially electrically non-conductive and non-ferromagnetic material known in the art, polycarbonate being one example of such materials. The magnet 112 need not provide a very high degree of homogeneity in the static magnetic field induced within the chamber 116. It is only necessary that any gradients in the static magnetic field within the chamber 116 be much less in magnitude than applied gradients that are induced by a gradient coil 120, the function of which will be explained below in more detail. In the embodiment shown in FIG. 11, the chamber 116 is a separate enclosure adapted to be easily inserted into and withdrawn from the enclosure 119, but other embodiments may use only the enclosure 119.

A radio frequency (RF) antenna 114 is disposed about the enclosure 119, typically on the exterior surface of the enclosure 119. In the present embodiment, the antenna 114 comprises a wire coil wound so that its turns lie in planes substantially perpendicular to the longitudinal axis of the chamber 116 and the enclosure 119. When pulses of RF electrical power are passed through the antenna 114, an RP magnetic field is induced within the chamber 116. Although described above in terms of coils, the antenna 114 can be configured in any other way as long as the RF magnetic field induced by the antenna 114 is substantially perpendicular to the static magnetic field induced by the magnet 112 within the volume defined by the enclosure 119. The RF magnetic field induces nuclear magnetic resonance phenomena in an object (not shown) disposed in the chamber 116, which phenomena themselves emit radio frequency energy detectable by the same antenna or a different RF antenna (not shown in FIG. 1) disposed near the chamber 116.

In the present embodiment, the antenna 114 performs both RF transmit and RF receive functions, and is coupled, through a coil section switch 126, to a Tx/Rx matching circuit and switch ("Tx/Rx switch") 128. The Tx/Rx switch 128 is under control of an acquisition and control system 134 or similar programmable controller configured to operate the Tx/Rx switch 128 such that the antenna 114 is selectively coupled to an RF power amplifier 136 during RF pulse transmission intervals, or to a receiver preamplifier 130 during NMR signal detection (receive) intervals. The input of the RF power amplifier 136 is coupled to the output of an RF driver 138. The input of the RF driver 138 is itself coupled to a pulse programmer 140. The pulse programmer 140 may be a separate element under control of a computer 142, or may be a function performed by the computer 142 itself.

The receiver preamplifier 130 output is coupled to the input of an RF receiver 132, the output of which is coupled to the acquisition and control system 134. The acquisition and control system 134 may include such circuits as analog to digital converters, digital filters and a recording device (not shown separately). The output of the acquisition and control system 134 is coupled to the computer 142 for analysis of voltages detected by the antenna 114 resulting from NMR phenomena in an object or body (not shown in FIG. 1) disposed in the chamber 116. The foregoing circuit elements, including the acquisition and control system 134, receiver preamplifier 130, Tx/Rx switch 218, computer 142, pulse programmer 140, RF driver 138 and RF power amplifier 136 can be of any type known in the art for generating, detecting and analyzing nuclear magnetic resonance signals.

The pulse programmer 140 is configured to operate the RF driver 138 to cause generation of a succession of selected length and selected frequency RF pulses through the antenna 114, such that NMR phenomena are induced in the object (not shown) disposed in the chamber 116. As is well known in the art, the frequency, amplitude and duration of the RF pulses are related to the amplitude distribution of the static magnetic field within the chamber 116, and to the gyromagnetic ratio of nuclei which are excited within the object (not shown) for NMR analysis.

The following components of the apparatus 110 are used to localize the excitation and detection of NMR phenomena within selected parts of the body being analyzed. The system 110 shown in FIG. 11 also includes the previously mentioned gradient coil 120 disposed outside the enclosure 119. The gradient coil 120 is configured such that when direct current (DC) of a selected magnitude is passed through the gradient coil 120, a known gradient magnetic field is superimposed on the static magnetic field induced by the magnet 112. In the present embodiment, the gradient is substantially linear and is directed along the longitudinal axis of the chamber 116. The amount of DC applied to the gradient coil 120 is controlled by gradient control 122, itself under operative control of the acquisition and control system 134.

The system 10 also includes a static field amplitude control coil 118 disposed outside the enclosure 19 and configured to induce a substantially homogeneous static magnetic field that is directionally aligned with the static magnetic field induced by the magnet 112. An amount of DC passed through the field control coil 118 determines an amount of change in the static magnetic field amplitude within the chamber 116. The amount of DC is controlled by a field control 124, which is also under operative control of the acquisition and control system 134. The total static field amplitude at any location in the chamber 116 is thus the sum of the amplitude of the field induced by the magnet 112, the gradient field induced by the gradient coil 120, and the additional static field induced by the field control coil 118.

Figure 12:
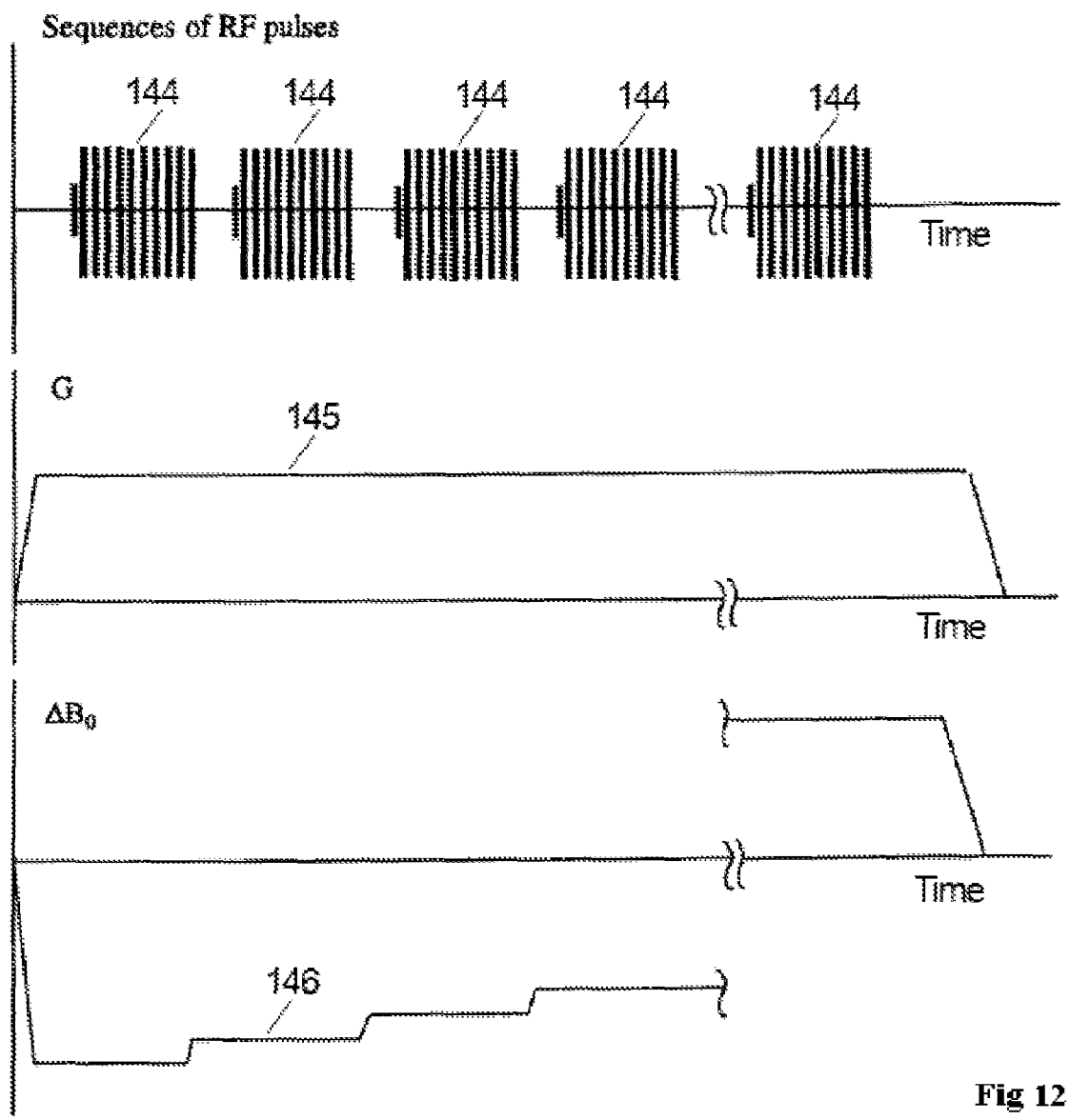
FIG. 12 shows RF pulsing sequences, gradient sequencing and static magnetic field amplitude control sequencing used with the apparatus of FIG. 11.

FIG. 12 shows graphs with respect to time of the various types of RF and DC power passed through the various antennas and coils of the apparatus of FIG. 11 so as to perform localized NMR excitation and measurement within selected portions of a body. RF pulse sequences are shown generally at 144 and are a representation of RF power passed through one or more sections of the antenna (114 in FIG. 11) to excite NMR phenomena and to detect NMR phenomena within a selected body portion. DC power passed through the gradient coil (120 in FIG. 11) is shown at 145. In one embodiment, the arrangement of the gradient coil and the magnitude of the DC 145 passed through the gradient coil is such that a defined gradient field is superimposed on the static magnetic field induced by the magnet (112 in FIG. 11). In some embodiments, the gradient field may be linear with respect to distance along a selected direction. The gradient field need not be linear, rather, it is only necessary for the gradient field to have a known spatial distribution. Finally, at 146, DC passed through the field control coil to adjust the amplitude of the static magnetic field is shown as providing time related different static field adjustment.

Figure 13:
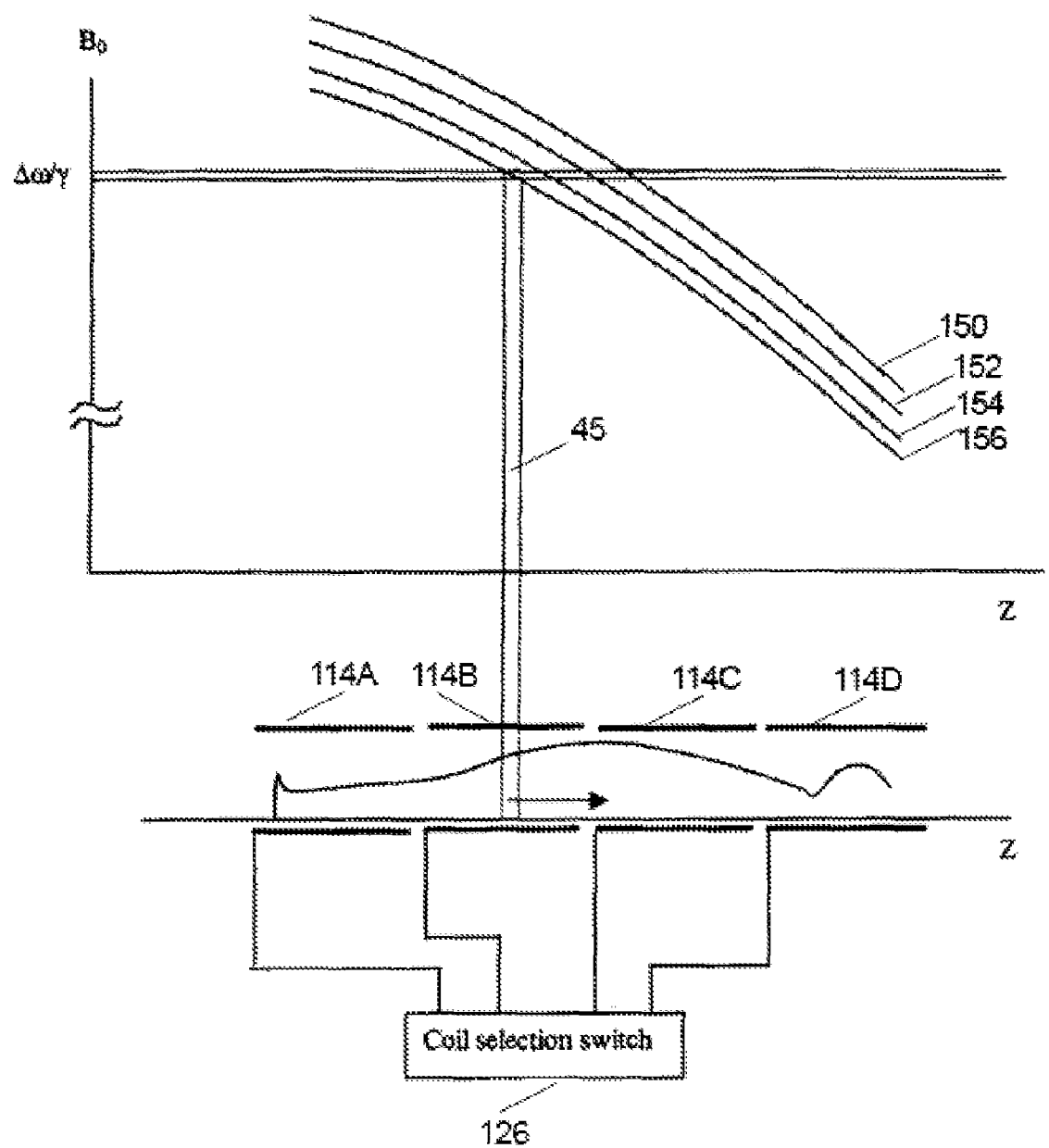
FIG. 13 shows the principle of the apparatus of FIG. 11 with respect to axial localization of NMR excitation and measurement.

The gradient field and static field adjustments to the static magnetic field from the magnet, shown graphically in FIG. 12, will result in NMR measurement localization as will now be explained with reference to FIG. 13. For each value of static field amplitude adjustment provided by the selected DC value passed through the field control coil (118 in FIG. 11), and considering the gradient field superimposed on the static magnetic field, a net static magnetic field amplitude with respect to position along a selected direction (in this case the longitudinal axis Z in the example of FIGS. 11-13) is shown by curves 150, 152, 154 and 156. For each such static field distribution, a different axial position (example axial "slice" 45 in FIG. 13) is defined along the body 44 for which NMR phenomena are excited and detected, because at these different positions, the total amplitude of the static magnetic field (sum of static, gradient and adjustment field amplitudes) is such that it matches the ratio of the radio frequency with respect to the gyromagnetic ratio of the nuclei being analyzed. The actual position and thickness of any "slice" will depend on the frequency and bandwidth of the RF system, as well as the gradient magnitude, as shown by ω/γ in FIG. 13. In the example of FIG. 13, the coil section switch 126 may select portions of the RF antenna, shown as 114A, 114B, 114C, and 114D to excite and detect NMR phenomena in the axial region proximate the particular "slice."

In the example embodiment of FIGS. 11-13, NMR phenomena may be excited in a first location or portion of the body 44. NMR measurements may be made for the excited body portion. Then, the field amplitude and/or gradient may be adjusted so as to move the position for NMR measurements to another body portion. The process may be repeated until measurements are made over the entire body. The NMR measurements may then be analyzed to determine composition of each of the body portions, and/or the entire body, as explained above with reference to FIGS. 6A-6D through FIG. 10.

The embodiment explained above with reference to FIGS. 11-13 is provided to illustrate the broad principle of a method according to the invention, in which NMR measurement and analysis is performed on localized portions of the body. It will be readily apparent to those skilled in the art that conventional NMR imaging apparatus known in the art, which can develop a fine resolution image of a body in volumes localized along three dimensions, may also be adapted to perform a method according to the invention. Accordingly, it is entirely within the scope of the invention to adapt a conventional NMR imaging apparatus to perform a method according to the invention.

Embodiments of a method according to the various aspects of the invention provide the ability to accurately and quickly evaluate whole body composition, even on conscious, live animals, without the need for very large, very expensive NMR spectroscopy or MRI instruments.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining the mass of at least one constituent of an entire body, comprising:
exciting a predetermined sequence of nuclear magnetic resonance (NMR) phenomena in the entire body;
measuring nuclear magnetic resonance (NMR) signals from the entire body;
composing at least a part of the measured signals from the entire body into a measurement vector;
calculating the mass of the at least one constituent without requiring an additional measurement from a predetermined function of the measurement vector, the predetermined function representing the at least one constituent and defining a standard for a range of at least one of compositional variations and temperature variations of the at least one constituent.

2. The method of claim 1 wherein the exciting nuclear magnetic resonance phenomena in the entire body comprises applying a plurality of sequences of pulsed magnetic fields having characteristics selected to produce sequences of NMR echoes which enable determining at least one of transverse relaxation properties and longitudinal relaxation properties of the at least one constituent of the body.

3. The method of claim 2 wherein the sequences comprise at least one Carr-Purcell-Meiboom-Gill sequence.

4. The method of claim 2 wherein a length of each of the sequences is selected to be related to a transverse relaxation time of the at least one constituent and at least one time delay between consecutive sequences is selected to be related to a longitudinal relaxation time of the at least one constituent.

5. The method of claim 1 wherein the predetermined function is derived from calibration measurement vectors composed from nuclear magnetic resonance signals obtained from calibration samples of known composition.

6. The method of claim 5 wherein at least one of the calibration samples represents the at least one constituent of the body.

7. The method of claim 6 wherein the calibration samples include at least two samples representing different compositional variations of the at least one constituent.

8. The method of claim 7 further comprising determining parameters of the distribution of the compositional variations of at least one constituent from the nuclear magnetic resonance measurements.

9. The method of claim 6 wherein the calibration samples include at least two samples representing the at least one constituent at different temperatures.

10. The method of claim 9 further comprising at least one of determining a temperature of the at least one constituent from the nuclear magnetic resonance measurements and determining a temperature distribution of the at least one constituent from the nuclear magnetic resonance measurements.

11. The method of claim 6 wherein at least one calibration sample representing fat tissue in the body comprises canola oil.

12. The method of claim 6 wherein at least one calibration sample representing lean body tissue comprises chicken muscle tissue.

13. The method of claim 12 wherein intrinsic compositional variation of samples of the chicken muscle tissue is compensated by using a plurality of chicken muscle tissue calibration samples.

14. The method of claim 6 wherein at least one calibration sample representing free body fluid comprises saline solution.

15. The method of claim 1 wherein the predetermined function of the measurement vector is linear, whereby the mass of the at least one constituent is determined as a scalar product of the measurement vector and a predetermined regression vector.

16. The method of claim 15 further comprising determining a set of regression vectors, each regression vector in the set corresponding to a different constituent of the body, and wherein the set of regression vectors is determined by approximating an arbitrary measurement vector by a linear combination of predetermined base vectors.

17. The method of claim 16 wherein at least one of the predetermined base vectors represents a single constituent of the body.

18. The method of claim 15 wherein the regression vector for each of the constituents is derived from calibration measurement vectors composed from nuclear magnetic resonance signals obtained on calibration samples of known composition.

19. The method of claim 18 wherein the determining the regression vector for each of the constituents comprises:
performing principal component analysis on a set of calibration measurement vectors;
selecting a set of significant principal components;
performing a partial least square fitting of the set of calibration measurement vectors by linear combinations of the selected set of significant principal components; and
calculating the regression vectors.

20. The method of claim 19 wherein the determining the regression vector for each of the constituents comprises normalization of each calibration measurement vector to the mass of the sample used to make the calibration measurements.

21. The method of claim 19 wherein the selecting the set of significant principal components comprises comparing eigenvalues of a calibration measurement covariance matrix corresponding to each principal component with covariance matrix eigenvalues of noise data.

22. The method of claim 19 wherein the selecting the set of significant principal components comprises determining errors of mass predictions for a set of test measurements.

23. The method of claim 19 wherein the set of significant principal components is selected by determining a degree to which measurement vectors of a test set of body parts are encompassed by a sub-space of the selected principal components.

24. The method of claim 19 wherein the set of significant principal components is selected by determining variability of the regression vector, regarding the components of a regression vector as values of a regression function of the component's sequential number and calculating the norm of the derivative of the regression function.

25. The method of claim 18 wherein the determining the regression vectors is preceded by smoothing of calibration measurement vectors, wherein the value of a vector component is set to be a piece-wise smooth function of the vector component number.

26. The method of claim 1, wherein parameters related to NMR measurement are selected to substantially localize NMR excitation within a body part, and further comprising:
selecting the parameters to localize NMR excitation within the different body part;
exciting a predetermined sequence of nuclear magnetic resonance phenomena in the different body part;
measuring nuclear magnetic resonance signals from the different body part;
composing at least a part of the measured signals from the different body part into a measurement vector; and
calculating the mass of the at least one constituent as a predetermined function of the measurement vector, the predetermined function representing the at least one constituent and defining a standard for a range of at least one of compositional variations and temperature variations of the at least one constituent.

27. The method of claim 26 further comprising repeating the localizing, exciting measuring, composing and calculating the mass of the at least one constituent in further different body parts until substantially the entire body is analyzed.

28. The method of claim 27 wherein the masses of the at least one constituent obtained in the different body parts are used to obtain the full mass of the at least one constituent in the body.

29. The method of claim 26 wherein the selecting parameters comprises superimposing a gradient magnetic field on a static magnetic field and adjusting an amplitude of the static magnetic field to move an NMR excitation volume along a direction of the gradient magnetic field.

* * * * *